(12) United States Patent
Lê

(10) Patent No.: US 10,952,887 B2
(45) Date of Patent: Mar. 23, 2021

(54) ORTHOPEDIC DEVICE, METHOD, AND SYSTEM FOR MAKING AN ORTHOPEDIC DEVICE

(71) Applicant: OSSUR ICELAND EHF, Reykjavik (IS)

(72) Inventor: Guillaume Lê, St. Etienne (FR)

(73) Assignee: OSSUR ICELAND EHF, Reykjavik (IS)

( * ) Notice: Subject to any disclaimer, the term of this patent is extended or adjusted under 35 U.S.C. 154(b) by 384 days.

(21) Appl. No.: 15/895,167

(22) Filed: Feb. 13, 2018

(65) Prior Publication Data

US 2018/0228635 A1 Aug. 16, 2018

Related U.S. Application Data

(60) Provisional application No. 62/458,066, filed on Feb. 13, 2017.

(51) Int. Cl.
*A61F 5/01* (2006.01)
*B33Y 80/00* (2015.01)
(Continued)

(52) U.S. Cl.
CPC .............. *A61F 5/0118* (2013.01); *A61F 5/01* (2013.01); *A61F 5/05866* (2013.01);
(Continued)

(58) Field of Classification Search
CPC ........ A61F 5/01; A61F 5/0102; A61F 5/0104; A61F 5/0118; A61F 5/05; A61F 5/058;
(Continued)

(56) References Cited

U.S. PATENT DOCUMENTS

| 2,477,126 A | 7/1949 | Hartmann |
| 3,955,565 A | 5/1976 | Johnson, Jr. |

(Continued)

FOREIGN PATENT DOCUMENTS

| CN | 105250062 A | 1/2016 |
| CN | 105250064 A | 1/2016 |

(Continued)

OTHER PUBLICATIONS

International Search Report from PCT Application No. PCT/US2018/017910, dated Aug. 1, 2018.

(Continued)

*Primary Examiner* — Keri J Nelson
(74) *Attorney, Agent, or Firm* — Workman Nydegger

(57) ABSTRACT

An orthopedic device comprises a body having a monolithic structure and arranged to form a closed circumference in a secured configuration, the body having a predetermined shape in an unsecured configuration. The body is formed continuously without interruption from at least one polymeric material. A method for making the orthopedic device includes providing a schematic including a model representing a body part for which the orthopedic device is intended, providing at least one array of coordinates and indicia corresponding to the coordinates proximate to the model at a plurality of locations along the model, and providing a scale set corresponding to the coordinates. The dimensions obtained from measuring the body part may be used to form a custom-shaped orthopedic device.

15 Claims, 15 Drawing Sheets

(51) Int. Cl.
  *B33Y 50/00* (2015.01)
  *A61F 5/058* (2006.01)
  *G06F 30/00* (2020.01)
  *A61B 5/107* (2006.01)
  *G06F 119/18* (2020.01)

(52) U.S. Cl.
  CPC .......... *A61F 5/05875* (2013.01); *B33Y 50/00* (2014.12); *B33Y 80/00* (2014.12); *G06F 30/00* (2020.01); *A61B 5/1077* (2013.01); *A61F 2005/0158* (2013.01); *G06F 2119/18* (2020.01)

(58) Field of Classification Search
  CPC .............. A61F 5/05841; A61F 5/05858; A61F 5/05866; A61F 5/05875
  USPC .............................. 602/21, 22; 128/878–880
  See application file for complete search history.

(56) References Cited

U.S. PATENT DOCUMENTS

| | | | |
|---|---|---|---|
| 5,063,613 A * | 11/1991 | Brown | A61F 5/05866 128/880 |
| 5,107,854 A | 4/1992 | Knotts et al. | |
| 5,539,649 A | 7/1996 | Walsh et al. | |
| 5,571,206 A | 11/1996 | Varn | |
| 5,776,088 A | 7/1998 | Sereboff | |
| 5,823,975 A | 10/1998 | Stark et al. | |
| 5,836,902 A | 11/1998 | Gray | |
| 5,911,126 A | 6/1999 | Massen | |
| 5,921,945 A * | 7/1999 | Gray | A61F 5/0585 128/882 |
| 6,177,034 B1 | 1/2001 | Ferrone | |
| 6,179,800 B1 | 1/2001 | Torrens | |
| 6,358,453 B1 | 3/2002 | Slemker et al. | |
| 6,463,351 B1 | 10/2002 | Clynch | |
| 6,597,965 B2 | 7/2003 | Graves et al. | |
| 6,725,118 B1 | 4/2004 | Fried et al. | |
| 6,840,916 B2 | 1/2005 | Kozersky | |
| 6,849,223 B2 | 2/2005 | Dean et al. | |
| 6,968,246 B2 | 11/2005 | Watson et al. | |
| 7,058,439 B2 | 6/2006 | Eaton et al. | |
| 7,097,799 B1 | 8/2006 | Burton | |
| 7,335,177 B2 | 2/2008 | Reynolds et al. | |
| 7,632,216 B2 | 12/2009 | Rahman et al. | |
| 7,797,072 B2 | 9/2010 | Summit | |
| 7,981,068 B2 | 7/2011 | Thorgilsdottir et al. | |
| 8,002,724 B2 | 8/2011 | Hu et al. | |
| 8,005,651 B2 | 8/2011 | Summit et al. | |
| 8,366,789 B2 | 2/2013 | Summit | |
| 8,417,487 B2 | 4/2013 | Summit et al. | |
| 8,423,167 B2 | 4/2013 | Sanders et al. | |
| 8,538,570 B2 | 9/2013 | Stanhope et al. | |
| 8,613,716 B2 | 12/2013 | Summit et al. | |
| 8,838,263 B2 | 9/2014 | Sivak et al. | |
| 8,978,224 B2 | 3/2015 | Hurley et al. | |
| 8,986,234 B2 | 3/2015 | Summit et al. | |
| 9,032,606 B2 | 5/2015 | Horkey | |
| 9,358,138 B2 | 6/2016 | Kelley et al. | |
| 9,529,941 B2 * | 12/2016 | Summit | A61F 5/01 |
| 2003/0032906 A1 | 2/2003 | Narula et al. | |
| 2004/0260402 A1 | 12/2004 | Baldini et al. | |
| 2005/0171461 A1 | 8/2005 | Pick | |
| 2006/0030802 A1 | 2/2006 | Nordt, III et al. | |
| 2007/0132722 A1 | 6/2007 | Kim et al. | |
| 2009/0146142 A1 | 6/2009 | Kim et al. | |
| 2009/0266362 A1 | 10/2009 | Mark | |
| 2009/0267261 A1 | 10/2009 | Mark | |
| 2010/0161076 A1 | 6/2010 | Pallari | |
| 2010/0268135 A1 | 10/2010 | Summit et al. | |
| 2011/0004074 A1 | 1/2011 | V et al. | |
| 2011/0009787 A1 | 1/2011 | Pallari et al. | |
| 2011/0115791 A1 | 5/2011 | Sabiston | |
| 2011/0301520 A1 | 12/2011 | Summit et al. | |
| 2011/0302694 A1 | 12/2011 | Wang et al. | |
| 2013/0150762 A1 | 6/2013 | Summit et al. | |
| 2013/0282141 A1 | 10/2013 | Herr et al. | |
| 2013/0310717 A1 | 11/2013 | Ranky et al. | |
| 2013/0317788 A1 | 11/2013 | Summit et al. | |
| 2013/0317789 A1 | 11/2013 | Summit et al. | |
| 2014/0012171 A1 | 1/2014 | Brown et al. | |
| 2014/0025183 A1 | 1/2014 | Kelley et al. | |
| 2014/0052039 A1 | 2/2014 | Summit et al. | |
| 2014/0142486 A1 | 5/2014 | Summit et al. | |
| 2014/0149082 A1 | 5/2014 | Sanders et al. | |
| 2014/0163697 A1 | 6/2014 | Sanders et al. | |
| 2014/0180185 A1 | 6/2014 | Zachariasen | |
| 2014/0188260 A1 | 7/2014 | Layman et al. | |
| 2014/0267116 A1 | 9/2014 | Weiner | |
| 2015/0088046 A1 | 3/2015 | Walborn et al. | |
| 2015/0105865 A1 | 4/2015 | Davis et al. | |
| 2015/0142150 A1 | 5/2015 | Layman et al. | |
| 2015/0216704 A1 | 8/2015 | Madden et al. | |
| 2015/0272764 A1 | 10/2015 | Kim et al. | |
| 2015/0290011 A1 | 10/2015 | Dudziak | |
| 2015/0290016 A1 | 10/2015 | Sommer | |
| 2015/0328016 A1 | 11/2015 | Summit et al. | |
| 2015/0328403 A1 | 11/2015 | Zachariasen et al. | |
| 2015/0352793 A1 | 12/2015 | Zukoski et al. | |
| 2015/0359644 A1 | 12/2015 | Sanders et al. | |
| 2015/0374051 A1 | 12/2015 | Rauckman et al. | |
| 2015/0374529 A1 | 12/2015 | Summit et al. | |
| 2016/0022466 A1 | 1/2016 | Pedtke et al. | |
| 2016/0045353 A1 | 2/2016 | Nayfa | |
| 2016/0058519 A1 | 3/2016 | Herr | |
| 2016/0058584 A1 | 3/2016 | Cespedes et al. | |
| 2016/0067062 A1 | 3/2016 | Jorgensen et al. | |
| 2016/0101572 A1 | 4/2016 | Schouwenburg et al. | |
| 2016/0171127 A1 | 6/2016 | Gannon et al. | |
| 2016/0192877 A1 | 7/2016 | Diez et al. | |
| 2016/0213320 A1 | 7/2016 | Shabah | |
| 2016/0235556 A1 | 8/2016 | Thompson, Jr. et al. | |
| 2016/0243762 A1 | 8/2016 | Fleming et al. | |

FOREIGN PATENT DOCUMENTS

| | | |
|---|---|---|
| CN | 205126526 U | 4/2016 |
| EP | 2671544 A2 | 12/2013 |
| WO | 2014148906 A1 | 9/2014 |
| WO | 2016071873 A2 | 5/2016 |
| WO | 2016170433 A1 | 10/2016 |

OTHER PUBLICATIONS

"3D Printed Cast Could Replace Plaster," Euronews, retrieved from www.euronews.com/2016/09/21/3d-printed-cast-could-replace-plaster, Oct. 4, 2017, pp. 1-3.

"Helping Through Innovation," Invent Medical, retrieved from www.inventmedical.com/, Oct. 10, 2016, pp. 1-11.

* cited by examiner

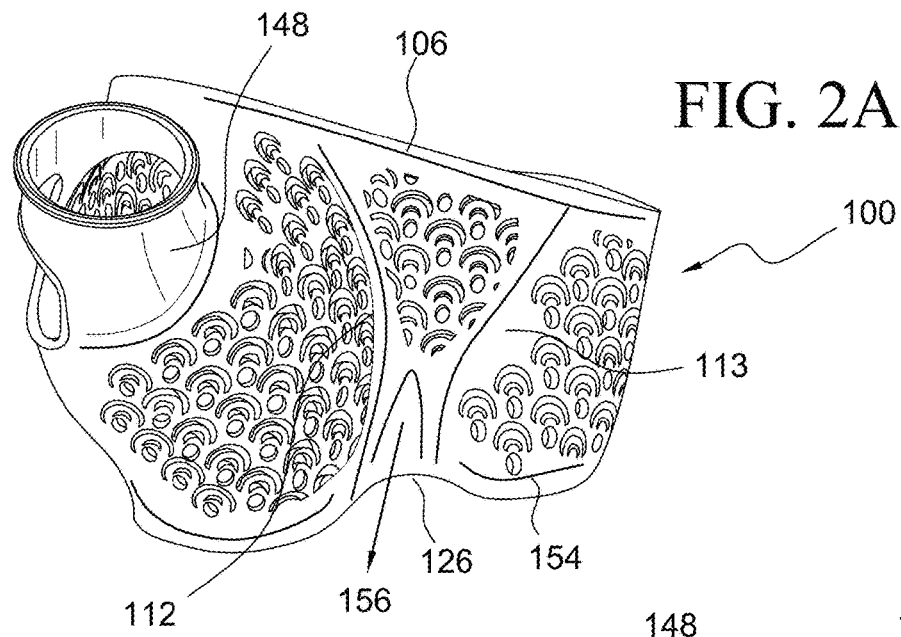
FIG. 2A
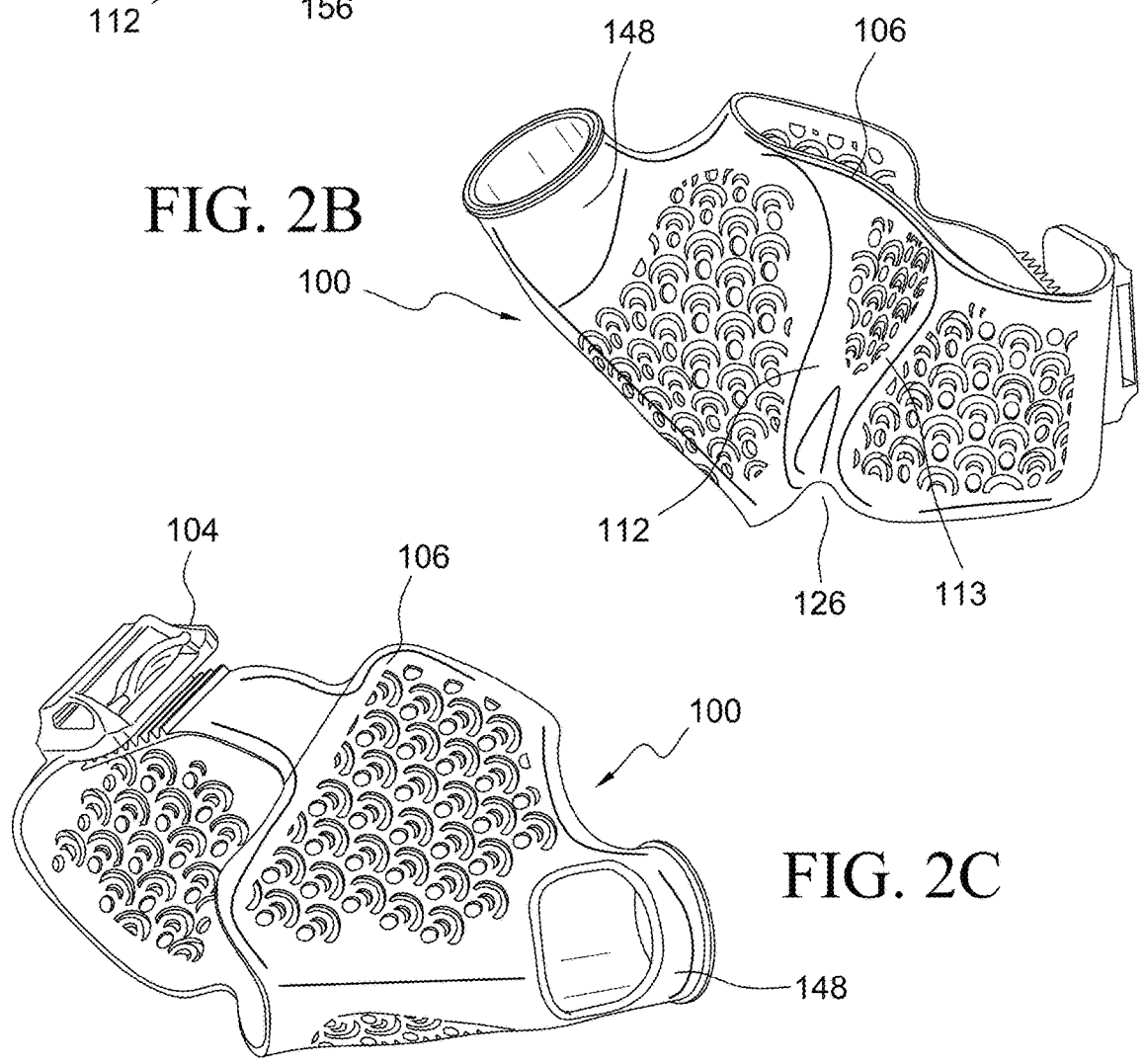
FIG. 2B
FIG. 2C

ORTHOPEDIC DEVICE, METHOD, AND SYSTEM FOR MAKING AN ORTHOPEDIC DEVICE

FIELD OF THE DISCLOSURE

The disclosure generally relates to orthopedic devices, and methods and systems for making orthopedic devices.

BACKGROUND

It is well known to create digital representations of orthopedic devices, including virtual fitting of a brace to a patient, prior to fabrication of an actual device. Many of these known systems offer solutions that may involve elaborate techniques including photogrammetry, image correlation, depth mapping, or any other suitable IR and/or visible light photography based surface topography detection method. From a three-dimensional representation of the body part topography, an orthopedic device is made having an inner surface that corresponds to the three-dimensional representation of the body part.

These solutions require expertise for properly obtaining the digital representation, according to the methods employed. Aside from the skill required to operate the equipment associated with creating the digital representation, such equipment is expensive and not readily available across a spectrum of healthcare providers. Limited use and time required to proceed with the process for creating the digital representation may not justify the acquisition of such equipment.

While it is desirable to obtain such digital representations of both a body part and corresponding brace, such as a hand and a hand brace, such representations may not clearly capture a true representation of a hand since the representations may erroneously include features of the body part that are not essential or complicate proper fitting of the brace on the body part (skin folds, wrinkles, skin lines, pannus, dimples, and other anatomical features unique to the intended user of the brace). These possibly flawed digital representations may compromise or corrupt the rest of the brace manufacture process.

Many types of conformal orthopedic devices are known, even those customized and devised from digital representations of a body parts. These known devices, particularly in hand braces, may lack sufficient angulation according to orthopedic parameters and customizations for a pathology of a user from which the digital representation is obtained. It is difficult to know the exact position a user's body part will take from merely a three-dimensional image scan, even if the software cleans the topography of the body part according predefined parameters.

If in a hand the thumb has a unique shape and orientation, and requires treatment from a brace, it is difficult to know from a picture, even a three-dimensional digital representation, how the thumb should be oriented while considering the unique shape. These known methods rarely account for pathologies and orthopedic rules, as the digital representation is not taken with such pathologies and rules in mind.

With current technology, it is relatively simple to print a three-dimensional orthopedic device, such as a hand brace, from a digital representation of a body. The difficulty lies in creating a digital representation according to parameters related to pathologies and orthopedic rules in mind, rather than merely obtaining a digital representation having generally accurate volume of a hand based on a cloud of points. The known digital representations are simply that: digital representations. It is not known to make such digital representations driven by essential parameters for addressing the pathologies and orthopedic rules.

An advantage to making a custom-fitted orthopedic device is that it can be tailor-made to the specific anatomy of a user, and with improved distribution pressure over the user's anatomy, to provide superior comfort without necessarily requiring padding. The configuration of the brace may provide a comfortable surface against the user's anatomy and possess a breathable wall structure.

It is a challenge in orthopedic devices to maintain braces on the user, and many known custom-fitted orthopedic devices lack integrated means for securing the brace on the user. Lack of comfort of the orthopedic device is a common drawback that disincentives or deters the user from wearing the brace according to the treatment plan prescribed by a clinician. Another difficulty lies in finding clinicians able to make such braces that provide the necessary quality and effectiveness needed to treat a wound. Despite improvements in comfort, fit, retention and breathability, users may not find braces aesthetically pleasing, further deterring use of the brace.

The production of one-of-a-kind custom-fitted braces can be a tedious and expensive process. Many custom-fitted braces are measured according to the clinician's experience, instruments or geographical region, and there is a lack of a standardized format for such measurement. There is a lack of uniformity in fabrication of custom-fitted braces, as each clinician relies on their individual skill and experience, which may vary among clinics. Few standardized processes are used for both measuring a user's affected anatomy and fabricating custom-fitted braces on a large scale, that involves geographical centralization of the process. There tends to be a delay in fabrication of such braces due to the customization and lack of standardization and centralization of the processes used to make the braces.

In view of these observations, there is a need for standardization of measurement that can be handled by clinicians and users internationally in a simple manner with a minimum of instruments, and a centralized, uniform, or systematic manufacturing process that can be executed in a timely manner to yield a custom-fitted brace for treating a user's affected anatomy.

From the foregoing, there is a need for a method and system for creating an orthopedic device that enables a generally accurate digital representation of a body part that does not have the attendant drawbacks of known methods and systems for creating a digital representation of a body part according to parameters associated with pathologies and orthopedic rules.

SUMMARY

According to embodiments described herein, orthopedic devices are described and arranged according to parameters related to pathologies and orthopedic rules in mind, rather than merely obtaining a digital representation having generally accurate volume of a hand based on a cloud of points. These embodiments are configured to be tailor-made to the specific anatomy of a user, and with improved distribution pressure over the user's anatomy, to provide superior comfort without necessarily requiring padding. While the embodiments share common characteristics or a pattern associated with human anatomy of an affected region, the embodiments are adaptable to such parameters unique to each user to provide a comfortable surface against the user's anatomy and to possess a breathable wall structure, while supporting the affected anatomy.

The embodiments may include integrated means for securing the orthopedic devices on the user in a comfortable and efficient manner. The embodiments possess improvements in comfort, fit, retention, and breathability, while offering the user choices to make the orthopedic devices aesthetically pleasing, and encouraging continual wear during a treatment plan.

In an exemplary embodiment, an orthopedic device comprises a body having a monolithic structure and arranged to form a closed circumference in a secured configuration, the body having a predetermined shape in an unsecured configuration. The body is formed continuously without interruption from at least one polymeric material.

In another exemplary embodiment, an orthopedic device comprises a body having a monolithic structure and arranged to form a closed circumference in a secured configuration. The body has a predetermined shape in an unsecured configuration. The body is formed continuously without interruption from at least one polymeric material. The body forms an opening bordered by first and second sides of the body. A strap assembly includes a strap depending from the first side of the body and arranged to extend across to the second side of the body and connect thereto to form the closed circumference. The body and strap assembly are formed continuously without interruption from a single piece of at least one polymeric material forming a homogenous structure.

In yet another exemplary embodiment, the orthopedic device consists a body having a monolithic structure and arranged to form a closed circumference in a secured configuration. The body has a predetermined shape in an unsecured configuration, and the body is formed continuously without interruption from at least one polymeric material. The body forms at least one fenestration region having a geometrical pattern with at least two fenestrations varying in size and/or dimension relative to one another. The body defines a band disposed about a periphery of the body, and the band encloses the at least one fenestration region. The body defines at least one rib extending from the band and adjacent to the at least one fenestration region. The at least one rib is devoid of fenestrations and defining a solid portion of material forming the body. The at least one rib being more rigid than the at least one fenestration region.

The features of these exemplary embodiments may be modified and combined with other features as described in the following description.

The methods described in this disclosure offer means for standardization of measurement of a user's anatomy that can be handled by clinicians and users in a simple manner with a minimum of instruments. It acknowledged that measurement means vary according to the location of the clinician and user; the methods of the disclosure offer a solution for standardizing the measurement process and a system enabling easy entry of the measurements and eventual fabrication of the orthopedic device.

Once the measurements are obtained and entered, the manufacturing process is generally centralized, uniform, or systematic and can be executed in a timely manner to yield a custom-fitted brace for treating a user's affected anatomy, but is nonetheless adaptable for actual fabrication and distribution of the orthopedic device at many geographical locations from the centralized system.

An exemplary method for measuring and making an orthopedic device includes the steps of: providing a schematic including a model representing a body part for which the orthopedic device is intended; providing at least one array of coordinates and indicia corresponding to the coordinates proximate to the model at a plurality of locations along the model; providing a scale set corresponding to the at least one array of coordinates; and taking measurements according to the at least one array of coordinates and indicia from an actual body part, and using the measurements to make a custom-fit orthopedic device. Additional steps and features concerning the exemplary method are described below in greater detail in the accompanying drawings and associated description.

The disclosure offers methods and systems for creating an orthopedic device that enable a generally accurate digital representation of a body part and which do not have the attendant drawbacks of known methods and systems for creating a digital representation of a body part according to parameters associated with pathologies and orthopedic rules.

These and other features, aspects, and advantages of the present disclosure will become better understood regarding the following description, appended claims, and accompanying drawings.

BRIEF DESCRIPTION OF THE DRAWINGS

FIGS. 2A-2C exemplify various perspective views of the hand brace of FIG. 1 exemplifying a frame to the hand brace.

Figure 1:
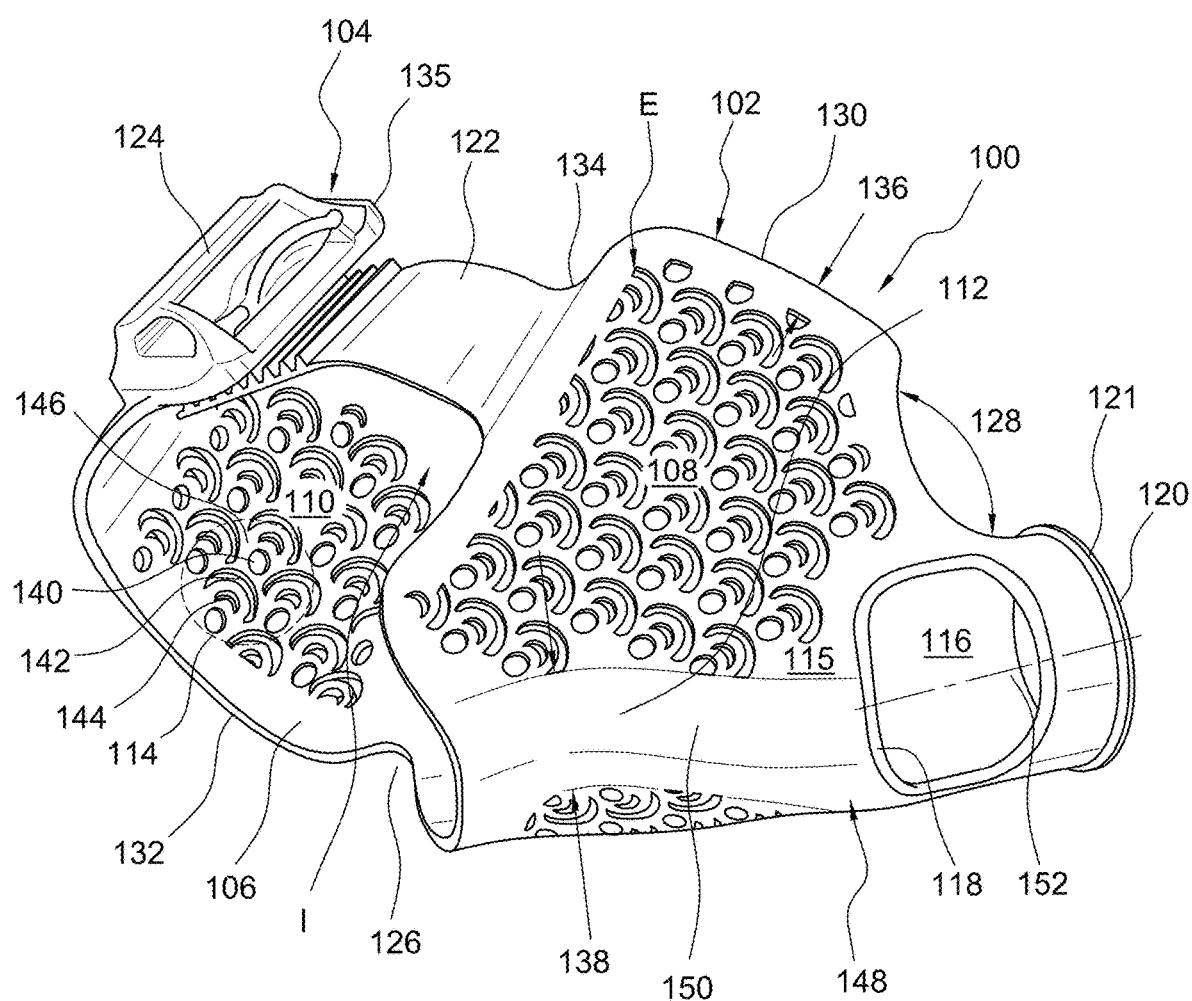
FIG. 1 is a perspective view of an embodiment of an orthopedic device in a hand brace.

The drawing figures are not drawn to scale, but instead are drawn to provide a better understanding of the components, and are not intended to be limiting in scope, but to provide exemplary illustrations.

DETAILED DESCRIPTION OF VARIOUS EMBODIMENTS

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and described below. It should be understood, however, there is no intention to limit the disclosure to the specific embodiments disclosed, but on the contrary, the disclosure covers all modifications, alternative constructions, combinations, and equivalents falling within the spirit and scope of the disclosure.

It will be understood that, unless a term is expressly defined in this disclosure to possess a described meaning, there is no intent to limit the meaning of such term, either expressly or indirectly, beyond its plain or ordinary meaning.

The disclosure generally relates to orthopedic devices, and discusses an example of such orthopedic devices in exemplary embodiments of a hand brace for treating complications of the hand, such as arthrosis/arthritis. Orthopedic devices for other body parts and indications may be constructed with features like those in the embodiment of the hand brace. Generally, the hand brace is conformal to a user's hand by closely corresponding to a digital representation and predetermined parametric of the user's hand. The sizing and extent of coverage of the hand brace over a user's hand may be determined during measuring and fabrication of the hand brace.

The hand brace is intended to be removable with a strap or fastening assembly for placing the hand brace in a closed circumference or loop forming a closed or secured configuration for retention on a user's hand, or in an open configuration for removal of the user's hand from the hand brace. It will be understood that by closed circumference, it is not intended that the hand brace be closed in its entirety, but rather at least a portion of the hand brace forms a closed circumference, such as by a strap and body of the hand brace.

Referring to FIG. 1, an orthopedic device 100 is in an exemplary form of a hand brace consisting a body 102 that is preferably formed as a single integrated structure from a structural material. The body 102 may be formed by additive manufacturing, three-dimensional printing machine, injection molding from a structural or composite material, such as a polymer or fiber reinforced material, combining polymer materials that are continuously molded together to be formed preferably without adhesives or fasteners, or by other suitable manufacturing techniques.

If there are multiple polymeric materials, they preferably have blended interfaces so that there is a transition of a first polymeric material to a second polymeric material, to avoid using separate adhesives or fasteners, but outside of the blended interface the first and second polymeric materials are distinctly separate from one another. In this example, different regions of the orthopedic device can be constructed from different polymeric materials suitable for structural areas (for example, rigidity), comfort (soft or harder materials), and other desirable properties.

Many materials can be used for making the orthopedic device, particularly those commonly used to print 3D objects, including but not limited to ABS plastic, PLA, polyamide (nylon), polypropylene and other thermoplastics, glass-filled polyamide, stereolithography materials (epoxy resins), silver, titanium, steel, wax, photopolymers and polycarbonate.

"Additive manufacturing" is understood as building three-dimensional objects by adding material layer-upon-layer. Common to additive manufacturing is the use of a computer, 3D modeling software (Computer Aided Design or CAD), machine equipment and layering material. Once a CAD drawing is produced, the additive manufacturing equipment reads in data from the CAD file and lays downs or adds successive layers of liquid, powder, sheet material or other material, in a layer-upon-layer fashion to fabricate a 3D object. The term additive manufacturing may encompass many technologies, including but not limited to subsets like 3D Printing, Rapid Prototyping (RP), Direct Digital Manufacturing (DDM), layered manufacturing, and additive fabrication.

In an exemplary embodiment, the body 102 entirely consists of the structural material in a continuous manner without interruptions in a homogenous structure of the body 102 formed by the structural material. As an alternative, the body 102 may be formed from different materials such as a first material forming a first region of the body 102 and a second material forming a second region of the body 102, however it is preferable that the first and second regions blend or are continuous with one another.

In yet another alternative, the structural material may be the same across the entirety or substantial entirety of the body 102, but may have different properties such as different resiliency, hardness, flexibility, or other desirable properties for a specified region. A first region may be heat treated or geometrically or dimensionally configured different from a second region. The first and second regions are formed from the same material but possess different properties.

The structural material may be rigid or semi-rigid, such that the body 102 conforms to the palmar and dorsal aspects of the user's hand, but retains its structure without yielding to movement of the hand when in the closed or secured configuration. The body 102 is sufficiently flexible to be tensioned over the affected area of the user as it is secured or placed in a closed configuration. The body 102 is resilient to return to a generally predetermined shape when the tension is released, and the body 102 or orthopedic device 100 is placed in an open or unsecured configuration, particularly during or over repeated uses. Additional features may be provided in combination with the body 102, such as straps, therapeutic elements such as heating or cooling elements, padding, and other known features in conventional orthopedic devices.

In the embodiment of FIG. 1, the body 102 preferably defines a strap assembly or enclosure device 104 adapted to place the body 102 in the secured configuration and in an open configuration. The strap assembly 104 is part of the monolithic and homogenous structure of the body 102, and is formed integrally with the remainder of the body 102 such that the strap assembly 104 is a unitary and continuous structure with the remainder of the body 102.

The body 102 defines a band 106 disposed about a periphery of the body 102, and the band 106 encloses at least one fenestration region 108, 110 defining a plurality of fenestrations formed by the body 102. The band 106 extends about an entirety of the body 102, including all peripheral sides enclosing the at least one fenestration region 108, 110, and merging with the strap assembly 104 on opposed sides of the body 102.

The body 102 defines at least one rib 112 extending from the band 106 and adjacent to at the least one fenestration region 108, 110. The at least one rib 112 is devoid of fenestrations and defines a solid portion of material forming the body 102. The at least one rib 112 extends between first and second opposed peripheral sides 130, 132 of the body 102. The first peripheral edge 130 may be deemed distal to or directed from or further away from the user's center of the body or torso, whereas the second peripheral edge 132 may be proximal because it may be closer to the user's center of the body than the first peripheral edge 130. The at least one rib 112 preferably merges into the band 106 along the first and second peripheral edges 130, 132. The at least one rib 112 has greater rigidity than the at least one fenestration region 108, 110, and preferably has rigidity greater than the band 106.

As depicted in FIG. 1, the at least one rib 112 preferably has a width 138 that is greater than a width 136 of the band 106, and the width of the at least one rib 112 may be variable depending on its location and its intended proximity to features of a human hand (i.e., joint, ligament, bone, nerves, etc.). The at least one rib 112 may have a thickness greater than the band 106. The at least one rib 112 may have a greater thickness than the at least one fenestration region 108, 110. While the body 102 may have a uniform thickness, it may alternatively have different or variable thicknesses. The band 106 may have a varying width about the periphery of the body 102 or a constant width.

In observing FIGS. 1-2C, the band 106 and the at least one rib 112, 113 define a frame 154 that extends around the at least one fenestration region 108, 110. The frame 154 includes a thumb column 148 for embracing and maintaining an orientation of a thumb. The frame 154 is substantially more rigid than the at least one fenestration region 108, 110. The frame 154 forms strength lines for the body 102 to maintain its shape and which border the at least one fenestration region 108, 110. The at least one rib 112, 113 includes first and second ribs 112, 113 merging into a joined region 156.

According to the depicted exemplary embodiment, the joined region 156 defines a widened region adapted to correspond to a carpal tunnel of user. A peripheral relief portion 126 corresponds to the joined region 156, and other peripheral relief portions may be provided according to the treatment of an individual user.

The at least one fenestration region 108, 110 defines a pattern 114 including at least one aperture or void 140, 142, 144. The at least one fenestration region 108, 110, allows air to circulate around the user's hand, while providing sufficient structural rigidity to support the user's hand. The at least one aperture 140, 142, 144 includes first and second apertures 140, 142 defining different shapes and/or dimensions. The at least one fenestration region 108, 110 defines a frame 146 separating the at least one aperture 140, 142, 144.

Referring to the embodiment of FIG. 1, the body 102 defines an opening 116 bordered by the at least one rib 112 and/or the band 106 and formed along a wall 115 of the body 102. The opening 116 is located outside the at least one fenestration region 108, 110, and has a size substantially larger than the at least one aperture 140, 142, 144. The opening 116 is arranged for coinciding with a metacarpal phalangeal joint.

For geriatric and/or arthritic users, the metacarpal phalangeal joint may be or appear pronounced over a healthy or normal joint. The joint may have an irregular shape and significantly vary from user to user, so rather than customize and measure the joint for every user, it may be expedient to provide the opening 116 to relieve the joint regardless of size variations. The rigidity of the hand brace 100, when worn, will significantly arrest the user's thumb, so a compromise of the irregular shape of the joint may be addressed while assuring that the thumb is retained in a fixed position, eliminating or reducing pressure on the user's joint and keeping it free from pain.

A thumb column 148 is sized and configured for supporting the thumb and arranging the thumb in a predetermined angulation relative to the remainder of the hand. The opening 116 may be located within a length of the thumb column 148. The body 102 may define a lip 118 about a periphery of the opening 116 and radially extending from and relative to the thumb column 148, to keep the opening 116 from any sharp edges and to offer enhanced strength about the opening 116 to prevent flexure of the thumb column 148. The lip 118 can have a greater thickness than the at least one rib 112 and/or the band 106. The thumb column 148 defines an outlet 120 from which a portion of a distal phalange of the thumb extends. The thumb column 148 may define a lip 121 extending about the outlet 120, and is bordered by the at least one rib 112 and/or band 106.

The thumb column 148 defines a first region 150 arranged for supporting a thumb metacarpal, and a second region 152 arranged for supporting a thumb proximal phalange including a metacarpal phalangeal joint. The opening 116 may be within the second region 152, or between the first and second regions 150 and 152. The first region 150 is preferably fixedly arranged at an angle different from an angle by which the second region 152 is fixedly arranged and different from the first region 150. The angle of the first region 150 is arranged to maintain the thumb metacarpal in a fixed position for abduction and flexion. The thumb column 148 may be fixedly arranged at an angle 128 relative to a remainder of the body 102 outside the thumb column 148.

The strap assembly 104 is integrally formed from the body 102 in that the body 102 and the strap assembly 104 are one and the same with one another and preclude attachments that are subsequently secured to the body 102. The strap assembly 104 includes a strap 122 depending from a third peripheral side 134 of the body 102. The strap 122 continuously extends laterally relative to the third peripheral side 134 and the band 106 located thereat in that the same material forming the band 106 extends into and forms the strap 122 without seams or interruption. The strap 122 is engageable with a bracket 124 carried by a fourth peripheral side 135 laterally opposed to the third peripheral side 134, and is generally located between the first and second peripheral sides 130, 132.

The bracket 124 is preferably integrally and continuously formed from the same material and structure forming the body 102. Alternatively, the bracket 124 may be adhered or otherwise connected to the body 102. Engagement of the strap 122 to the bracket 124 places the body 102 in a closed or secured configuration because an exterior E of the body 102 forms a continuous circumference, loop, or closed shape without interruption. Disengagement of the strap 122 from the bracket 124 places the body 102 in an open configuration because access is provided into an interior or interior surface I of the body 102.

Figure 2D:
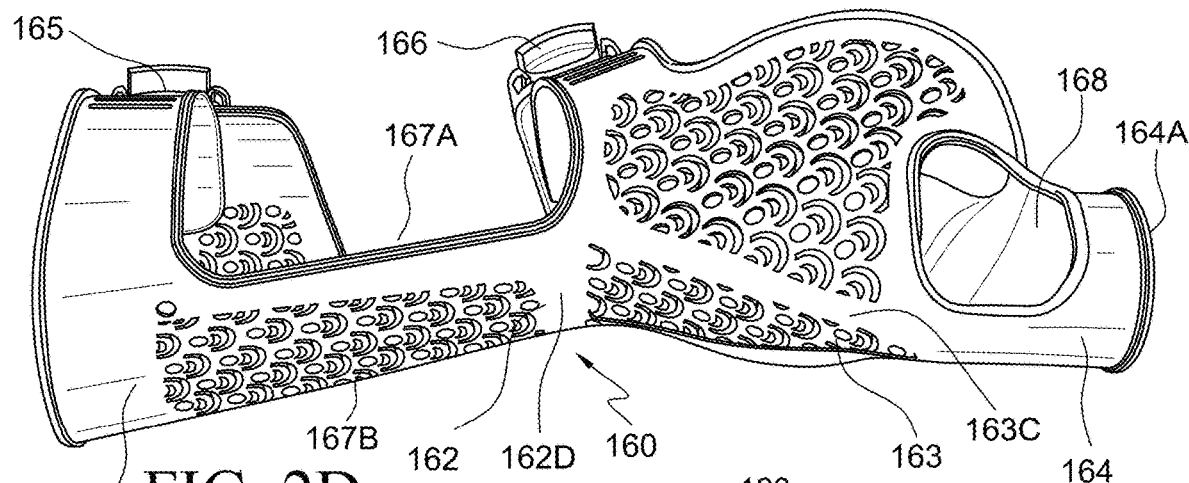
FIGS. 2D-2F exemplify various perspective views of a variation of the hand brace of FIG. 1.
Figure 2E:
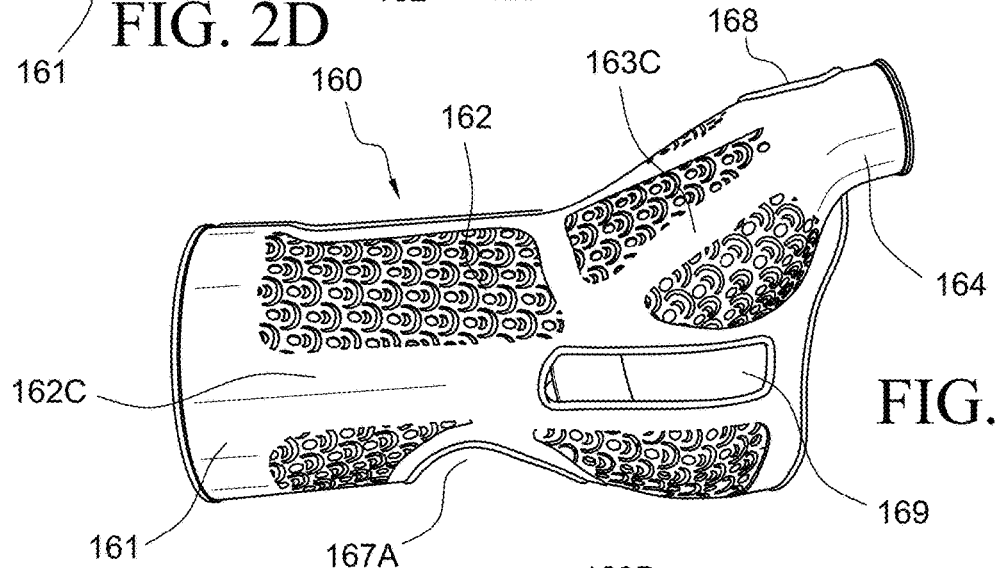
Figure 2F:
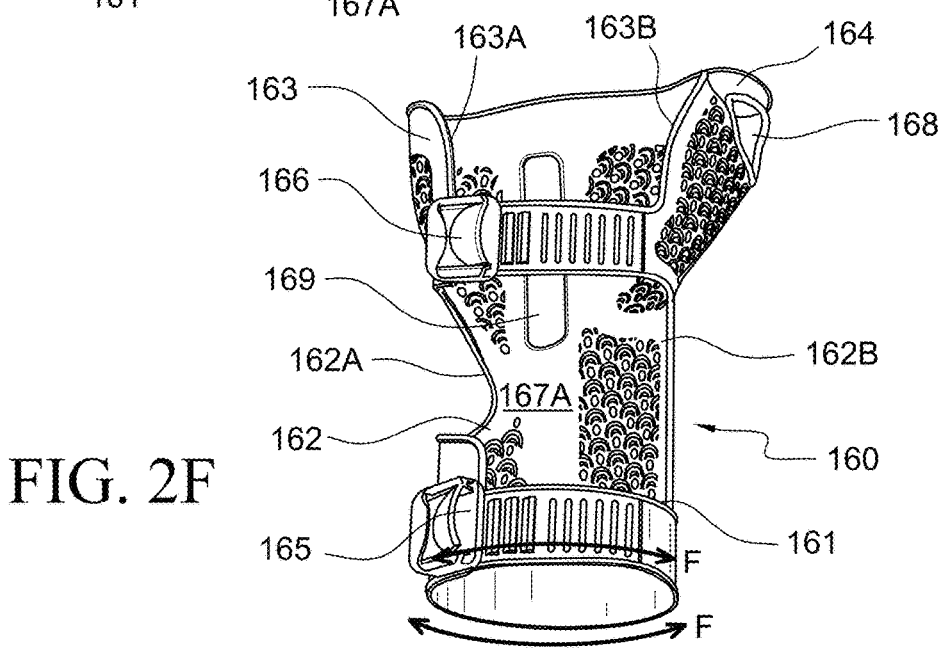

FIGS. 2D-2F illustrate another exemplary embodiment of an orthopedic device 160 in the form of a forearm/wrist brace made according to the methods and principles disclosed herein, since the wrist brace 160 is selectively adapted to provide enhanced support, such as along the forearm. The wrist brace 160 includes a forearm portion 161, a wrist portion 162, a hand portion 163 and a thumb portion 164 having a thumb hole 164A. The wrist brace 160 includes at least two integrally formed strap assemblies 165, 166, as discussed similarly in associated with the strap assembly 104 of FIG. 1, arranged to move edges 162A, 162B of the forearm and wrist portions 161, 162 relative to one another, and edges 163A, 163B of the hand portion relative to one another.

The wrist brace 160 may be selectively provided with openings, aside from fenestration regions, that are adapted in areas of the wrist brace that do not require additional support. A forearm opening 167A is provided along the forearm portion 161, yet a forearm support 167B is likewise provided proximate the forearm opening 167A to assure stabilization of the forearm, while maintaining the opening 167A. The forearm opening 167A may be along the dorsal aspect of the forearm, and the forearm support 167B may be along the ventral aspect, to provide enhanced support. A similar opening 169 may be located along the dorsal aspect of the hand portion 163. The thumb portion 164 may have an opening 168 to relieve the joint or a nerve, and serves as an example of how these openings 167A, 168, 169 may be selectively and optionally provided during the ordering and fabrication of the orthopedic device 160.

In addition to the fenestration regions, the orthopedic device 160 may define reinforcement sections or ribs 162C, 162D, 163C that extend in predetermined areas where additional reinforcement is required. During the ordering process of the orthopedic device 160, these reinforcement sections 162C, 162D, 163C may be optional and selected depending on the areas of the patient requiring reinforcement, or they may be predetermined as default areas of the wrist brace 160. The reinforcement sections 162C, 162D, 163C may be adjusted depending on the measurements once entered and fabricated for a custom-fitted orthopedic device for an individual user.

FIG. 2F exemplifies by arrows F how the body of the wrist brace 160 may be semi-rigid because the body is arranged to flexibly conform and tension about a user because of tensioning of the strap assembly 165 to place the orthopedic device 160 in the secured configuration, by drawings the edges 162A, 162B toward one another. When in the secured configuration, both the structure, such as by the band, ribs, and fenestrations, each imparting structure yet flexibility and breathability to the body, and the inherent qualities of the material the body, such as the material being a polymeric material that may be with or without fiber reinforcement or other reinforcement, do not yield to movement of a user over which the body extends. Once the strap assembly 165 is released, however, the tension about the user's hand is reduced and the body may resiliently return to a predetermined shape corresponding to an open and unsecured configuration, which the body was in prior to being in the closed or secured configuration.

The apertures of the at least one fenestration region 108, 110 may define different patterns that may be uniformly or irregularly defined. The frame of the at least one fenestration region 108, 110 maintains sufficient rigidity throughout the at least one fenestration region 108, 110, and enhances the overall rigidity and support of the hand brace 160 in combination with the at least one rib 113 and band 106. While the at least one fenestration region 108, 110 depicted in the illustrated embodiments are shown the same in each region, the orthopedic device 160 may be provided with differently shaped or sized fenestration regions with apertures differently shaped according to the region, to modify ventilation and breathability characteristics and biomechanical features of the orthopedic device 160. The at least one fenestration region 108, 110 lightens the orthopedic device 160 by providing ventilation and breathability to provide enhanced comfort for the user. Further, the user may have an option to select among different patterns to allow for aesthetic options, which may encourage the user to wear the orthopedic device throughout the duration of treatment by allowing for personalization of orthopedic device 160.

Figure 3A:
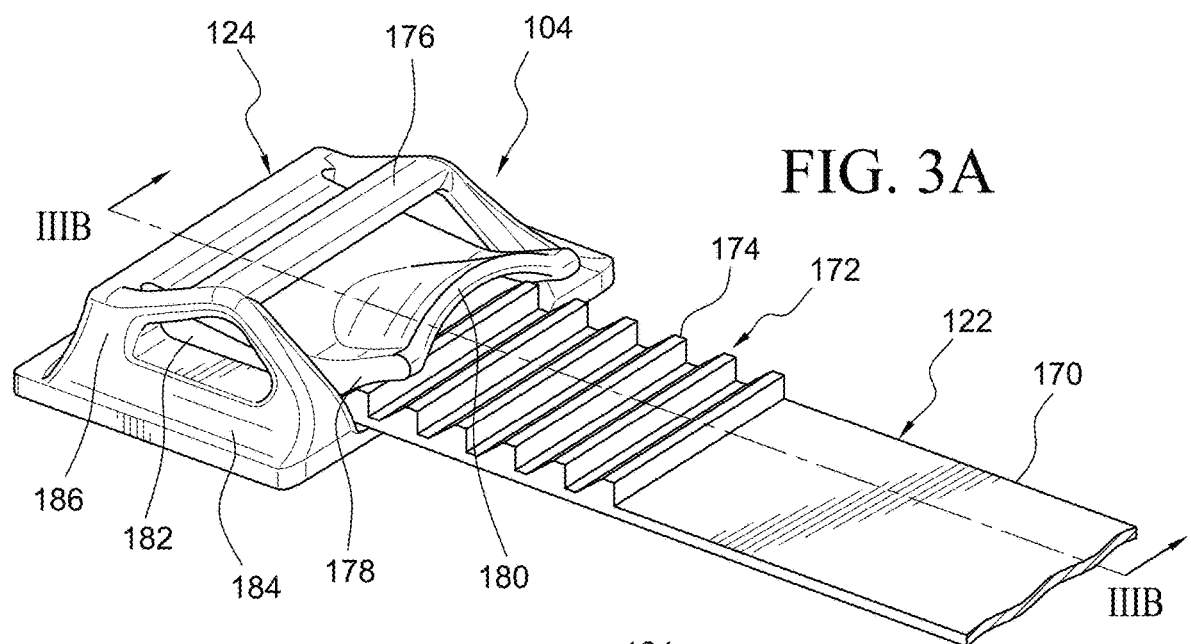
FIG. 3A is a perspective view of a strap assembly in the hand brace of FIG. 1.
Figure 3B:
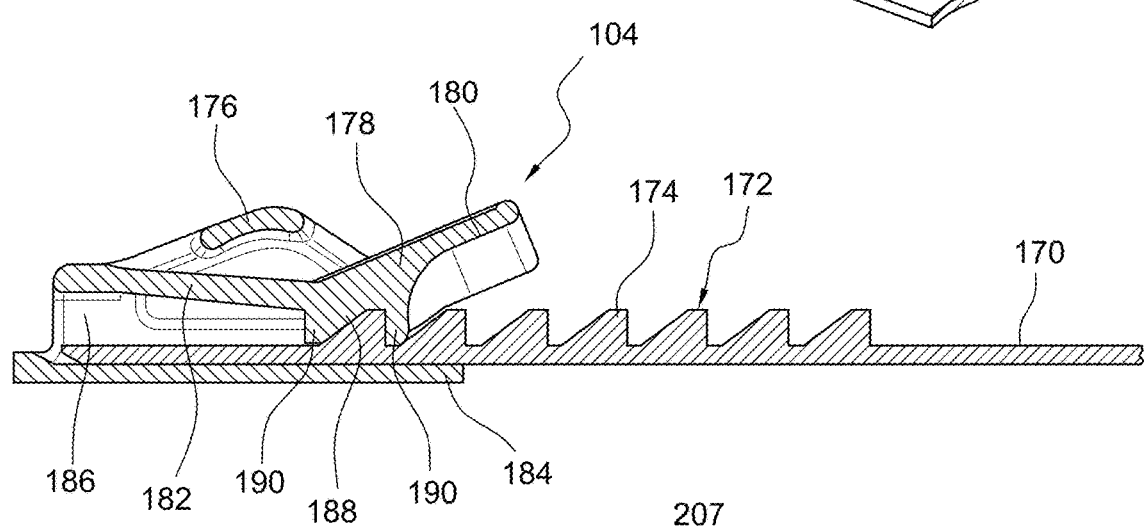
FIG. 3B is a cross-sectional view taken along line IIIB-IIIB in FIG. 3A.

Referring to FIGS. 3A and 3B, the strap 122 includes a base 170 having an elongate form, a plurality of teeth 172 formed transversely along the base 170, with each tooth of the plurality of teeth 172 having a tip 174. The bracket 124 includes upper and lower portions 176, 184 between which a latch 178 is flexibly suspended and biased for engagement with at least one of tooth of the plurality of teeth 172. The bracket 124 further defines a rear portion 186 extending between and connected to the upper and lower portions 176, 184 and from which an arm of the latch 178 extends. The latch 178 is biased from the rear portion 186 and towards the lower portion 184.

The latch 178 is movable between the upper and lower portions 176, 184. The latch 178 defines a tab 180 having an arcuately recessed profile and attached to a latch arm 182. The tab 180 is shaped to accommodate a thumb for lifting the tab 180 upwardly toward the upper portion 176 away from the strap 122. The latch 178 forms a detent profile 188 having a pair of teeth 190 adapted to engage one tooth of the plurality of teeth 172, the detent profile 188 arranged to surround opposed sides of the tip 174 of the corresponding tooth of the plurality of teeth 172. The plurality of teeth 172 defines a serrated profile, and the detent profile 188 corresponds in shape to the serrated profile of the plurality of teeth 172. The bracket 124 may be monolithic and formed from the same material without interruptions or seams, or may be separately formed and adhered or otherwise connected to the body of the orthopedic device 100.

Figure 3C:
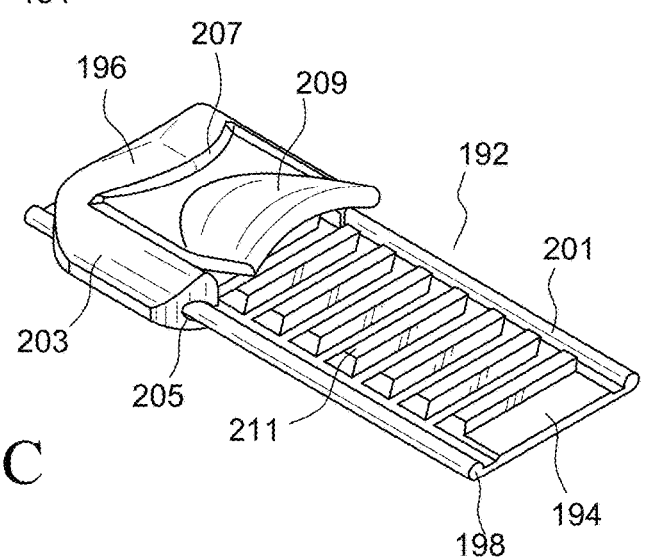
FIG. 3C is a perspective view of another strap assembly embodiment.

FIG. 3C exemplifies another exemplary embodiment of a strap assembly 192 that may be similarly formed with and/or connected to the orthopedic device 100. The strap assembly 192 includes a strap 194 that slides within a bracket 196. The strap 194 has a cross-sectional profile 198 forming opposed ribs 201 alongside portions of the strap 194. The bracket 196 defines opposed side portions 203 which form channels 205 into which the ribs 201 slide for stabilizing and directing movement of the strap 194 relative to the bracket 196. The bracket 196 defines a tab 209 depending from a rear portion 207 and arranged for engaging a plurality of teeth 211 carried by the strap 194 that may be arranged in a manner like the strap assembly of FIGS. 3A and 3B. Like the latch 178 of FIGS. 3A and 3B, the tab 209 may have an arcuately recessed profile configured for receiving a user's thumb or finger.

Figure 4:
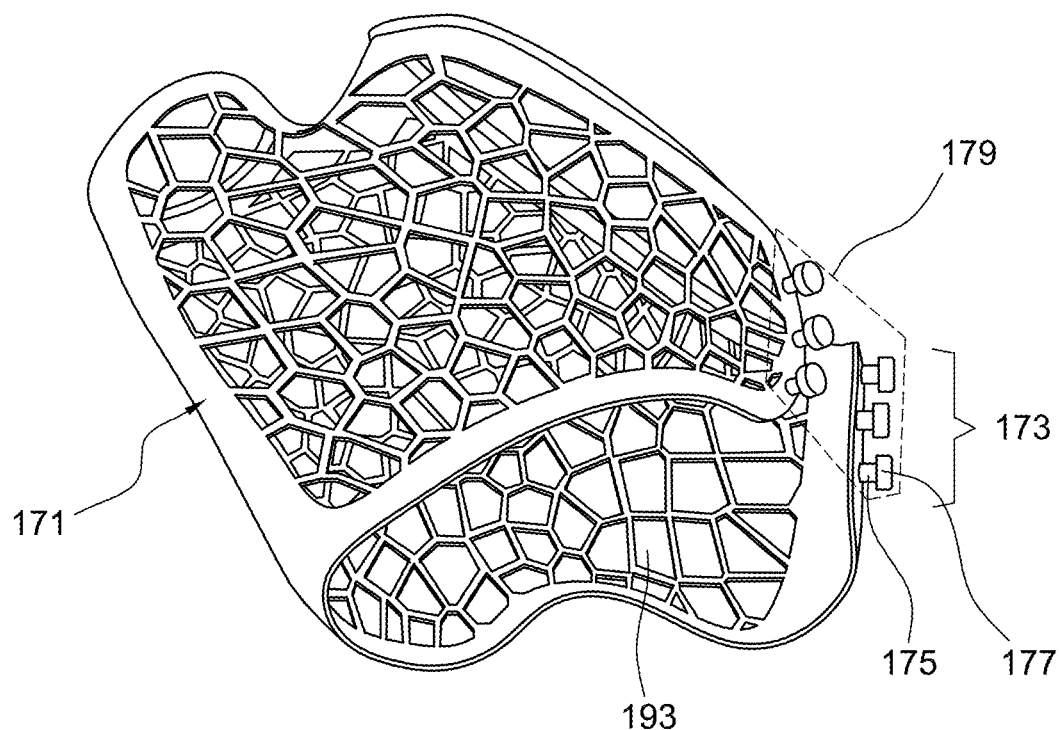
FIG. 4 is a perspective view showing a variation of the hand brace of FIG. 1.

FIG. 4 exemplifies another exemplary embodiment 171 of a hand brace including first and second sets of locking tabs 173 located on opposed sides of a frame of the hand brace 171, and a strap 179 is engageable with the first and second sets of locking tabs 173 to bridge a distance between the first and second sets of locking tabs 173. Each of the locking tabs 173 defines a stem 175 and a head 177 for engagement with corresponding structure on the strap 179, such as openings adapted to receive and engage the head 177.

Figure 5:
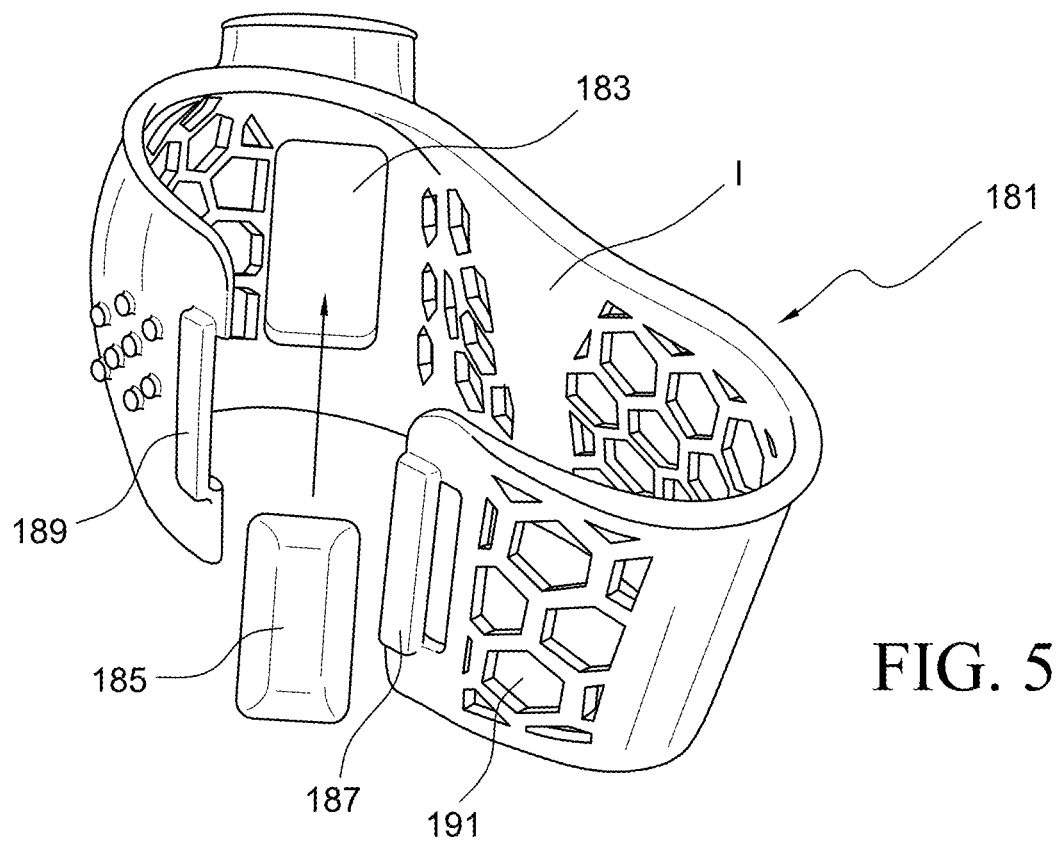
FIG. 5 is a perspective view showing another variation of the hand brace of FIG. 1.

FIG. 4 shows a variation of a fenestration region having a geometrical pattern 193 with apertures varying in size and/or dimension depending on their location at the body, exemplifying an irregular geometrical pattern (such as a Voronoi pattern or diagram) of apertures. FIG. 5 shows a fenestration region having a geometrical pattern 191 with apertures a uniform size and/or dimension regardless on their location at the body.

FIG. 5 depicts another exemplary embodiment of the hand brace 181 wherein the body defines strap loops 187, 189 formed from the body for receiving a strap. FIG. 5 exemplifies how any of the embodiments of the orthopedic device may have an exterior or interior surface for receiving therapeutic elements. The hand brace 181 defines a recess 183 adapted to receive a therapeutic element 185 and is configured for being located generally flush with the body of the device 181.

Figure 6A:
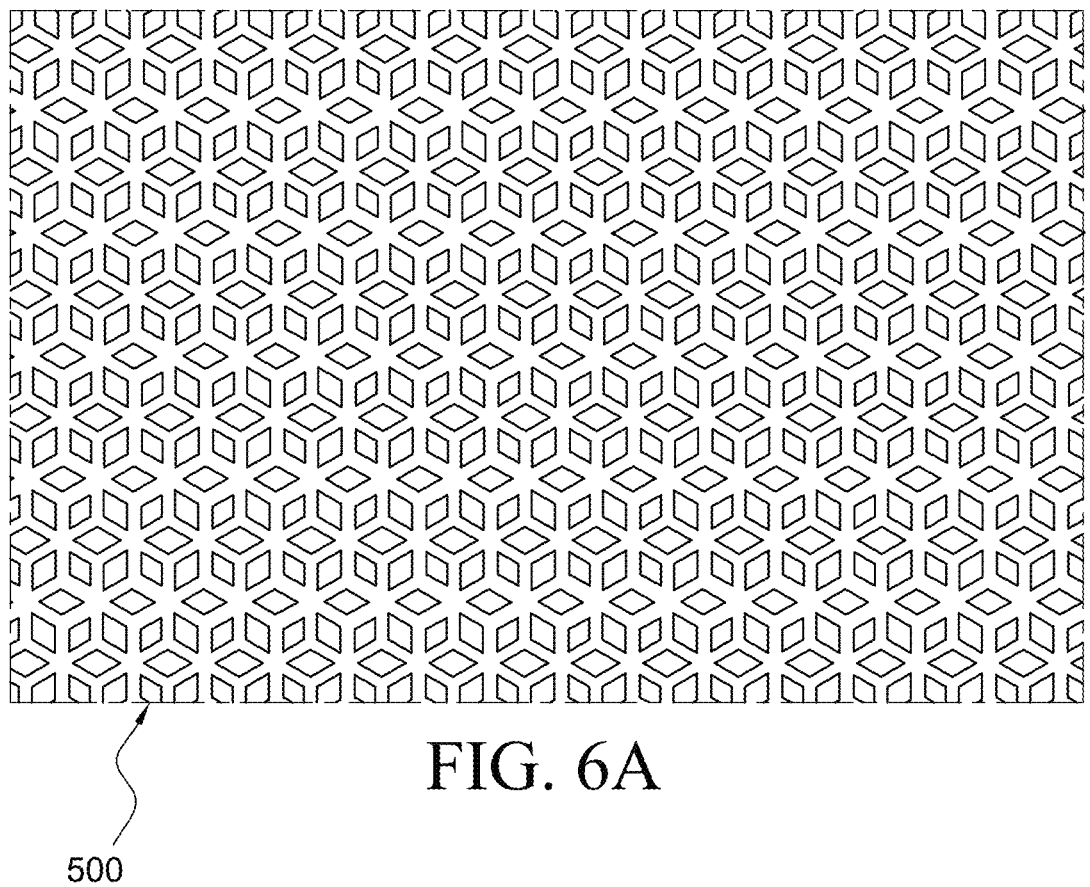
FIG. 6A is an exemplary view of a fenestration pattern.
Figure 6B:
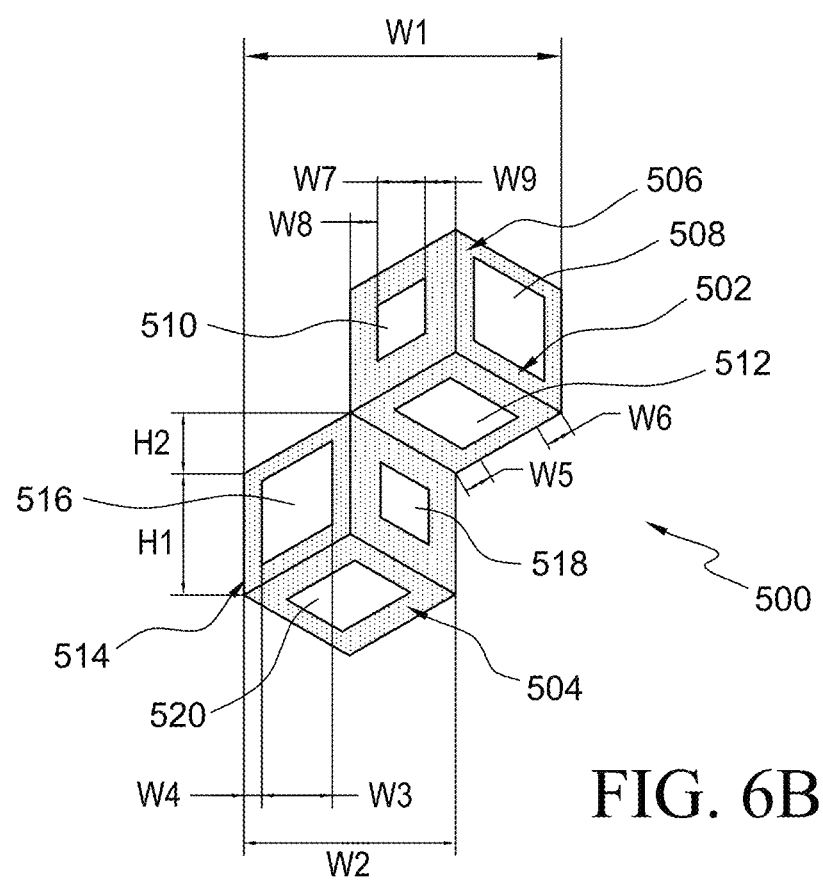
FIG. 6B is an exemplary view showing apertures in the fenestration pattern of FIG. 6A useable in the hand brace of FIG. 1.

Referring to FIGS. 6A and 6B, a sample of a fenestration region 500 has a geometrical pattern forming first and second cube sets 502, 504 having alternating orientations relative to one another. Each of the first and second cube sets 502, 504 forms a frame 506, 514 surrounding at least three apertures 508, 510, 512, 516, 518, 520, respectively, having varying sizes. The frame 506, 514 has a width that is generally the same although the at least three apertures 508, 510, 512, 516, 518, 520 vary in size. In this manner, the frame 506, 514 provides generally uniform support despite the at least three apertures 508, 510, 512, 516, 518, 520 being different in size and location. The frame 506, 514 may have varying widths to achieve biomechanical, functional and aesthetic purposes.

For example, a first width w1 comprises the entire width of a pair of first and second cube sets 502, 504. A second width w2 represents the width of cube 504, which comprises a fourth width w4 of a frame element of frame 514 and a third width w3 of aperture 516. The fourth width w4 may vary from fifth and sixth widths w5, w6 corresponding to the cube set 502, as necessary to achieve desired functions and dimensions. First and second heights H1, H2 of frame 514 similarly may be chosen based on the dimensions of widths w1, w2, w3, w4, w5, w6 and to achieve desired functions and dimensions. Likewise, a seventh width w7 of aperture 510 relates to an eighth width w8 of a frame element of frame 506 and a ninth width w9, which may be varied to achieve desired functions and dimensions.

The fenestration region 500 of FIGS. 6A and 6B offers a visual aspect or appearance of three dimensional cubes that enhances a three-dimensional impression, and offers a desirable balance between material and vacuity. The balance is achieved in that if there is too much vacuity and air, the fenestration region 500 will become fragile. If there is too much material in the pattern, the fenestration region 500 may fail to provide significant advantages as being insufficiently flexible.

Figure 7:
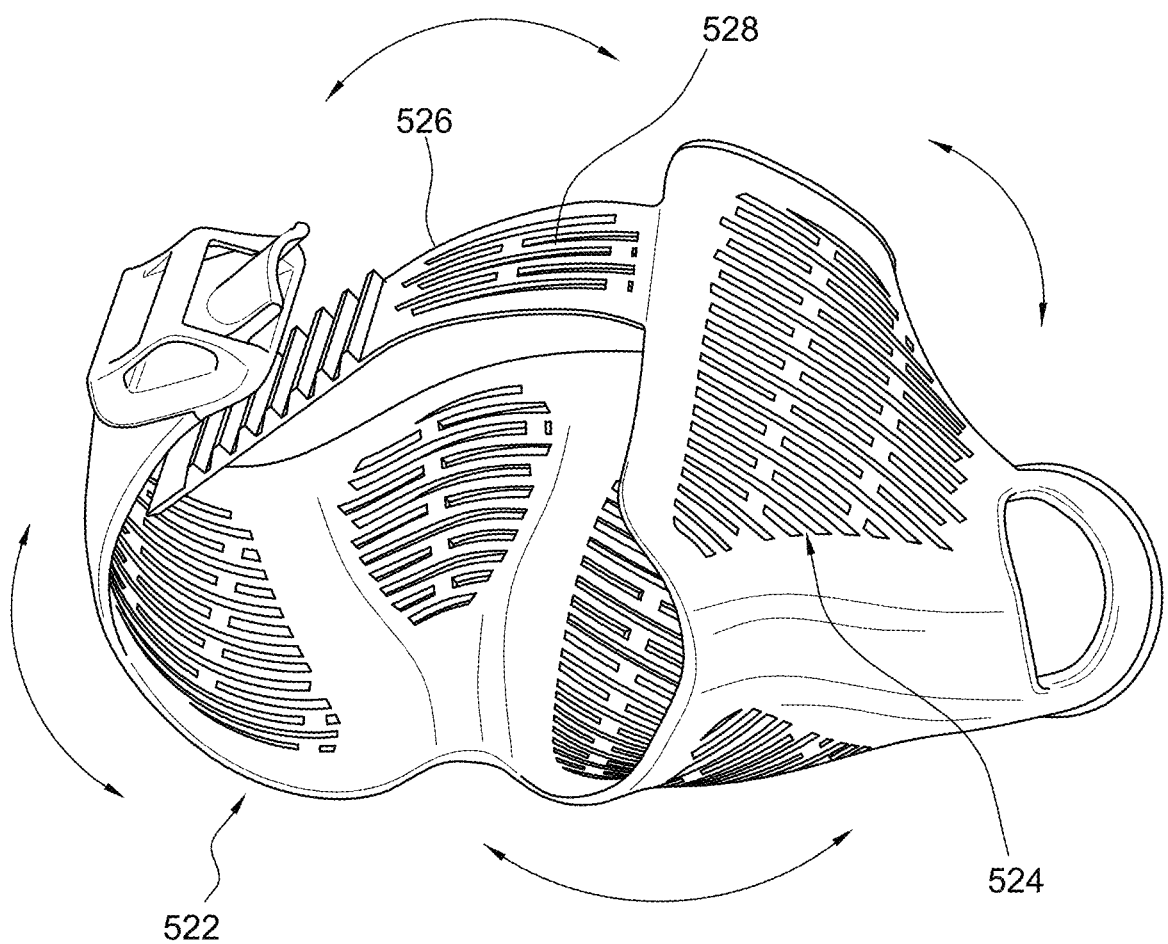
FIG. 7 is a perspective view showing another variation of the hand brace of FIG. 1 with a functional fenestration pattern.

FIG. 7 depicts how a hand brace 522 has at least one fenestration region 524 offering functionality by facilitating movement or fitting of the hand brace 522. Fenestration region 524 defines elongate apertures 526 generally arranged laterally relative to the hand to improve flexibility and tightening of the hand brace 522 about the hand, as evidenced by arrows about the hand brace 522. Further, a strap 528 includes the elongate apertures 526 in a fenestration region along its length to improve its flexibility when wrapping about the user's hand. The fenestration region 524 along the strap 528 may be used in combination with other fenestration regions having the same or differing geometrical patterns, each having functionality selected based on where the fenestration region is located on the hand brace 522.

The fenestration region 524 is arranged to lay flat on the interior side or surface corresponding to the palmar and dorsal surfaces of the user. However, a variation of the fenestration region 524 may include an exterior side or side that may define various heights protruding or extending from the flat interior side or surface of the hand brace 522, such as in the fenestration pattern 500 in the exemplary embodiment of FIGS. 6A and 6B. Such varying heights may further enhance the strength of the hand brace 522 and offer additional functionality such as enabling discrete regions of enhanced flexibility, stiffness, or other desired frame properties imparted into the monolithic body of the hand brace 522.

Figure 8A:
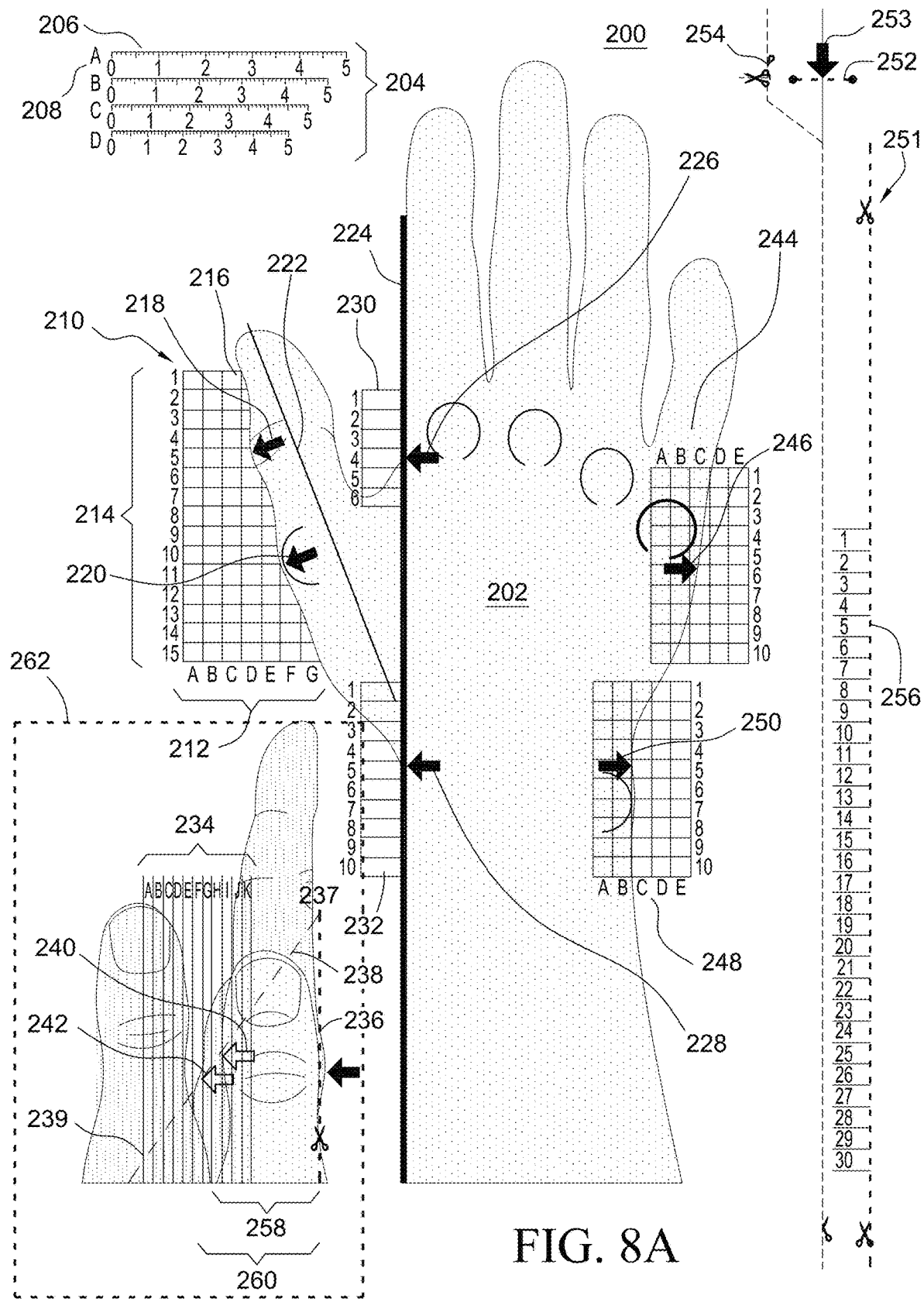
FIG. 8A is an exemplary schematic for measuring dimensions for forming the hand brace of FIG. 1.

FIG. 8A illustrates a schematic or measurement form 200 that may be used for measuring anatomical portions to create an accurately dimensioned orthopedic device, such as the embodiments of the hand brace. Unlike prior art methods for creating a digital representation of a user's body part based on the methods discussed above, the schematic 200 offers a device, methodology, and system that is easy to use, less complex, and cost effective. The schematic 200 relies on taking measurements at predefined locations of a model 202, such as one generalized as a hand in FIG. 8A. The measurements are used to create a parametric model of the user's hand while advantageously accounting for the irregularities and pathologies unique to the individual user in fabricating the orthopedic device.

The schematic 200 may be printed on paper, displayed on a suitable electronic display, or shown via any other suitable medium. If printed on paper, then a clinician or user needs only a writing implement, a ruler, and scissors.

The schematic 200 includes the model 202 representing a body part for which the orthopedic device is intended. The schematic 200 further includes at least one array of coordinates 210 and indicia 212, 214 corresponding to the coordinates proximate to the model 202 at a plurality of locations along the model 202. A scale set 204 corresponds to the at least one array of coordinates 210. Each of the coordinates 210 includes at least one locator 216 comparable to an actual body part relative to the model 202 for which the custom-fit orthopedic device is intended to treat and be worn. When using the schematic 200, the at least one locator 216 may be marked on the schematic 200 based on a location of the actual body part relative to the model 202 in the array of coordinates 210.

The size and shape of the at least one array of coordinates 210 may vary according to the location in the schematic 200. For example, the array of coordinates 210 for measuring the thumb is both longer and wider than the array of coordinates 230, 232 for measuring between the thumb and index finger, or where the thumb transitions to the wrist. The array of coordinates 210 for measuring the thumb is likewise a different dimension than the array of coordinates for measuring the hand proximate the little finger 244 and the base of the hand 248. As with the difference in size of the array of coordinates 210, the indicia 212, 214 may be designated along horizontal and vertical axes, respectively, however sometimes only the vertical axis is needed, as in the array of coordinates 230, 232.

As the scale of the schematic may vary depending on how a clinician receives the schematic 200, the scale set 204 is provided to approximate the actual size of the user's hand. The scale set 204, upon receipt for fabrication of the orthopedic device, can be compared to actual dimensions of an actual ruler to ascertain according to the indicia 208, among the at least one scale 206, to which scale the measurements can be indexed. The at least one scale 206 may be set to roughly five centimeters, and when fabrication is desired, the actual dimension of a ruler is measured against the at least one scale 206 and the correct indicia is chosen to scale up the schematic 200. In this manner, a clinician can print the schematic 200 on different sized media, anywhere in the world. Essentially, the locators 216 are not tied specifically to a dimension, rather they are provided relative to the scale set 204.

The schematic 200 displays at least one alignment target 218, 220, 226, 228, 240, 242, 246, 250 corresponding to a feature common to body parts such as an index finger of a hand. When comparing a user's hand to the model 202, the clinician may align the actual hand to the at least one alignment target 218, 220, 226, 228, 240, 242, 246, 250. At least one of the locators 216 corresponding to the at least one alignment target 218, 220, 226, 228, 240, 242, 246, 250 is marked according to the location of the actual body part. The schematic 200 displays at least one reference line 222, 224 over the model 202 for locating/placing the actual body part relative to the reference line 222, 224. The at least one alignment target 218, 220, 226, 228, 240, 242, 246, 250 corresponds to the at least one reference line 222, 224.

The schematic 200 defines a region 262 for measuring the thickness of the hand, finger(s), and thumb. The region 262 is defined by cut boundary 237 and baseline 236, and includes a generally diagonal cut-line 239 along which at least one positioning line 238 is formed. A triangle, shown as 257 in FIG. 8E, is removed from the region 262, and essentially from the schematic 200, by cutting along the cut-line 239 and at least a baseline 236. The hand, finger(s), or thumb can be inserted into the removed triangle void. The baseline 236 is aligned with a dorsal side of an actual hand and the thickness of the hand, finger(s) and thumb is obtained according to where at least one of the alignment targets 240, 242 intersects one of the plurality of sizing lines 234. The baseline 236 and at least one positioning line 238 may be used for comparing at least two portions of the body part relative to one another, as noted above. The at least one positioning line 238 is arranged obliquely relative to the baseline 236, and the at least one alignment target 240, 242 is located along the at least one positioning line 238.

The schematic 200 displays at plurality of sizing lines 234 indexed incrementally away from the baseline 236. The baseline 236 corresponds to the dorsal side of a hand, and the plurality of sizing lines 234 enable measurement of a thickness 258 of a thumb and a thickness 260 of a hand, such that the plurality of sizing lines 234 extends toward the palmar side of a hand.

The schematic 200 defines a region 251 having an elongate scale 256 for measuring a circumference or distance about a portion of a body part. The region 251 includes at least one cutting line 254 for removing the region 251 from the schematic 200. The elongate scale 256 includes a slit or baseline 252 for measuring a length of the circumference or distance about the portion of the body part. The slit 252 enables the elongate scale 256 to extend therethrough for measuring a circumference of a wrist.

The schematic 200 may be provided on a single sheet of paper or similar medium. The schematic 200 can be provided on differently sized mediums without impeding its usability. A clinician in the U.S.A. can print the schematic 200 on a standard sheet of paper of 8.5×11 inches (216×279 millimeters), and a clinician in Europe can obtain the schematic 200 on an A4 sized medium 210×297 millimeters (8.27×11.69 inches). The scale set 204 enables a determination of an approximation of how the locators 216 should be measured in actual dimensions.

The schematic 200 may be printed or formed so it is non-language specific. This is advantageous in that the schematic 200 can be used in different countries without the necessity of printing different languages thereon.

FIGS. 8B-8F exemplify possible steps for making measurements of a wrist and hand in view of the schematic 200, considering the features provided by the schematic 200.

Figure 8B:
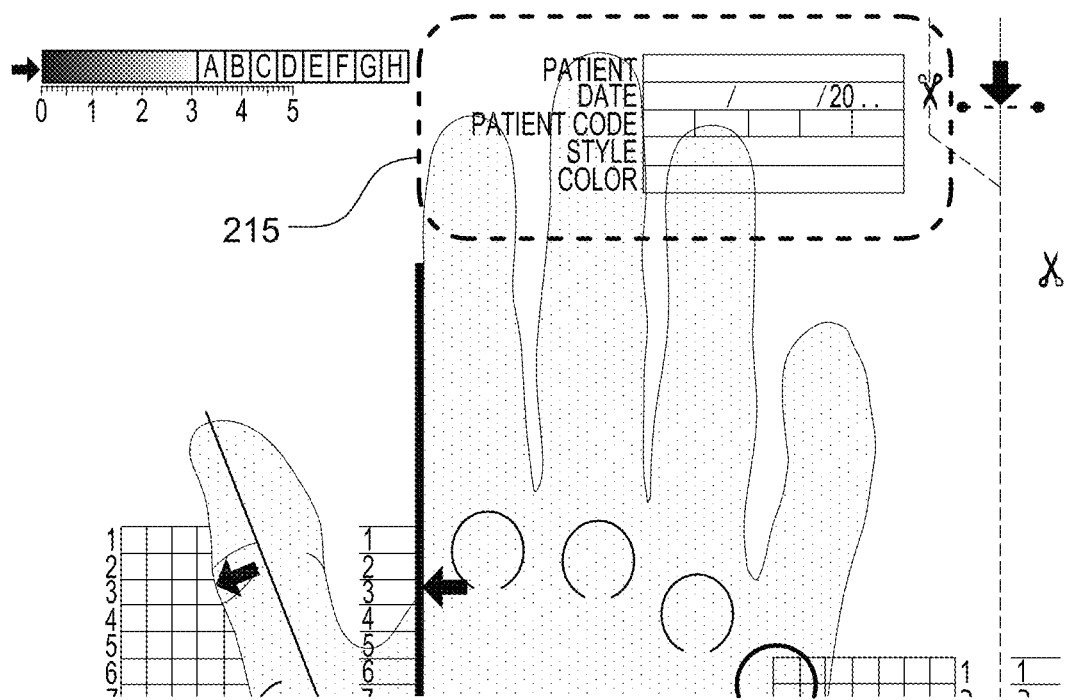
FIG. 8B is an exemplary step of entering personal information in the schematic of FIG. 8A.

FIG. 8B shows a step of filling out at least one field with the user information. The field 215 may also specify the type of orthopedic device desired for fabrication. While the schematic 200 is directed to measuring a hand, different wrist or hand braces may be obtained by the schematic 200. This may include a brace for supporting a thumb while permitting wrist movement, and the thumb and wrist support, or only wrist support. The field 215 may be useable if it is scanned for entry into a system for ordering the orthopedic device.

Figure 8C:
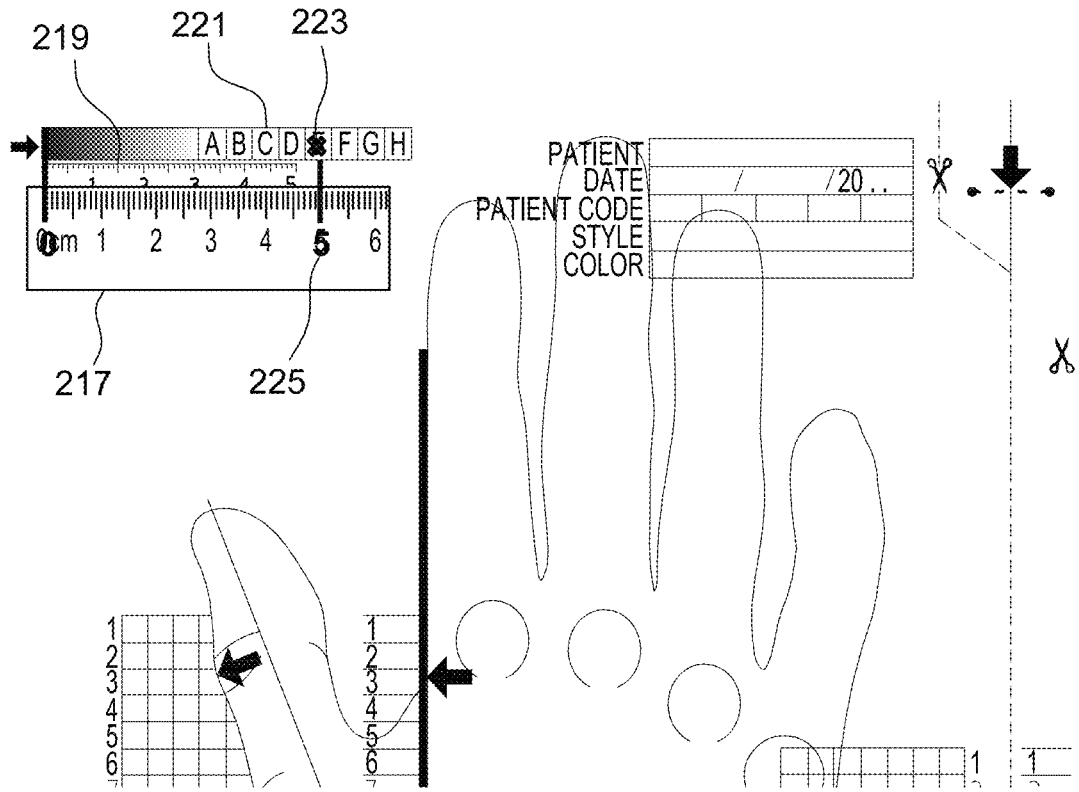
FIG. 8C is an exemplary step of gauging the dimensions of the schematic of FIG. 8A versus a ruler.

FIG. 8C shows a step of measuring or gauging the scale of the schematic 200 versus a ruler 217 for determining relative dimensions. Since the schematic 200 may deviate from the actual size or length in which it was published, it is necessary to determine the scale of the schematic 200 versus actual dimensions of a ruler 217, establishing the relative dimension of the schematic 200 to actual dimensions of a ruler 217. In this step, the ruler 217 is compared to a scale set 219 representing the dimension of a ruler that must be compared to the schematic 200. The scale set 219 resembles 5 cm which is compared to alignment locators 221 on the schematic 200. Once the scale target dimension 225 of 5 cm is compared to the alignment locators 221, the appropriate box 223 of the locators is selected as a comparison of what the schematic 200 considers the dimension versus the actual linear measurement of the ruler 217 at the target dimension 225.

Figure 8D:
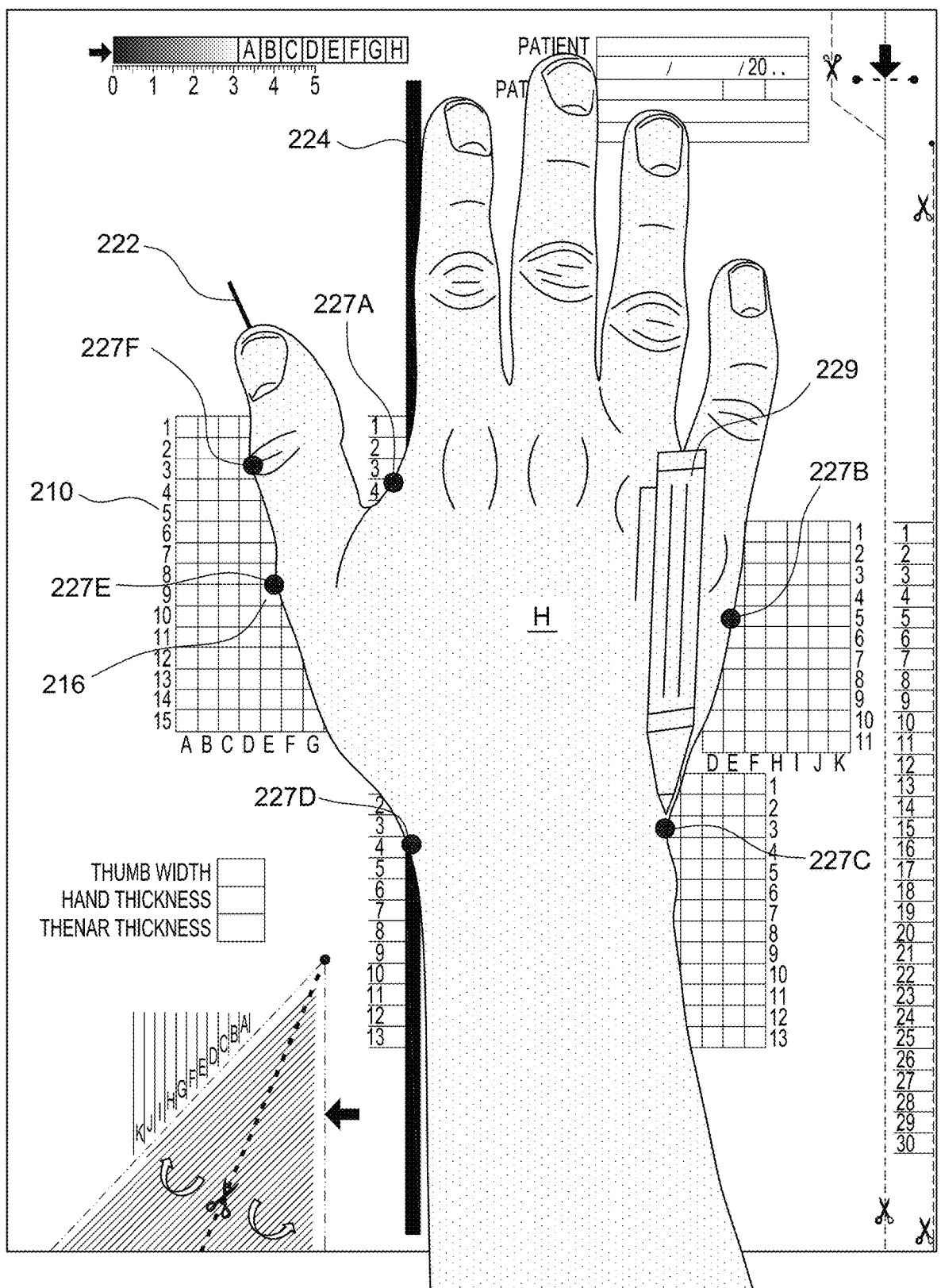
FIG. 8D is an exemplary step of marking predetermined parts of a hand against the schematic of FIG. 8A.
Figure 8E:
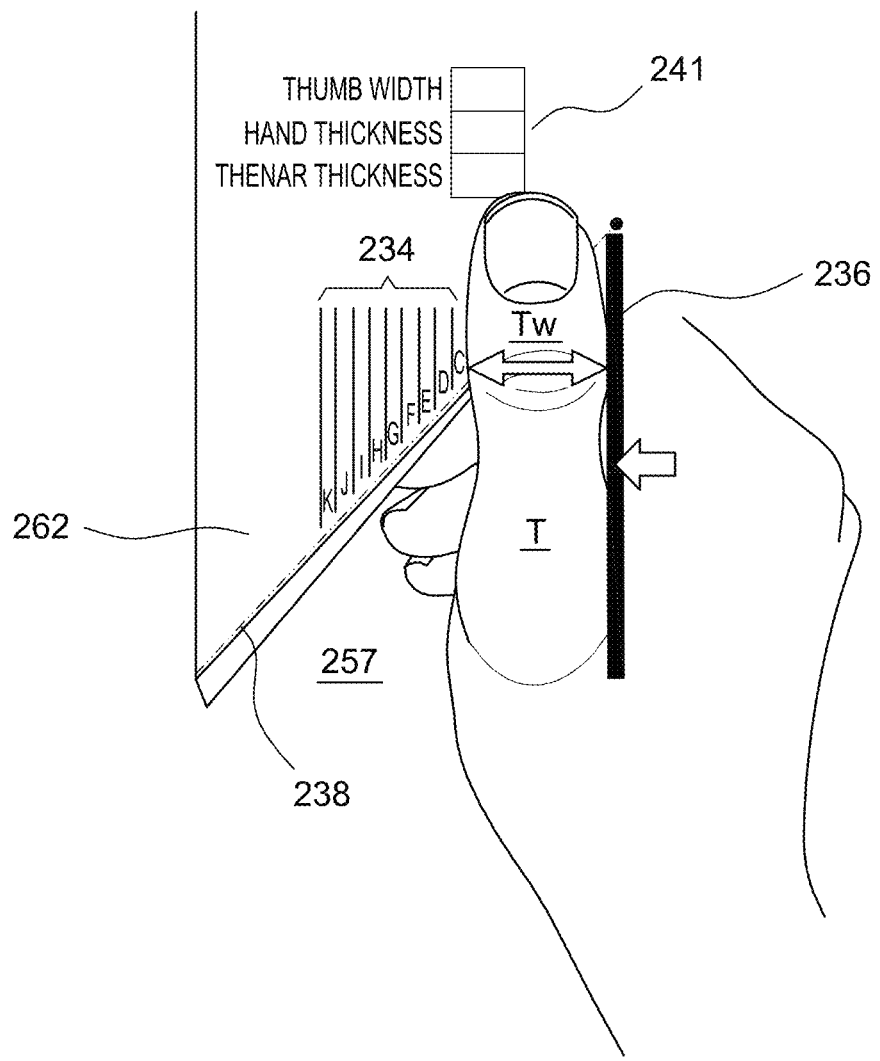
FIG. 8E is an exemplary step of measuring a thickness of a thumb against the schematic of FIG. 8A.

FIG. 8D shows measuring a hand H aligned to the at least one alignment target 218, 220, 226, 228, 240, 242, 246, 250 in FIG. 8A. The hand H is aligned with the reference line 222 and the reference line 224. Markings 227A-227F are placed in the arrays of coordinates 210 at corresponding locators 216 by a writing implement 229. Each of the locators 216 is indexed to coordinates 210, such that locators 216 can be entered by the clinician when ordering the orthopedic device. This process enables the ordering of the orthopedic device to easily determine where strategic locations of the measured hand are found, without the necessity of numerous measurements, but rather simply by transposing the hand of the schematic according to the reference line 222 and reference line 224.

FIG. 8E shows measuring the thumb T of the user according to region 262. The thumb T is placed within the triangle 257 and placed against the base line 236. The thickness Tw of the thumb T is determined between the base line 236 against the sizing lines 234 along the at least one positioning line 238. The thickness of the thumb T is placed in a measurement field 241 on the schematic 200. The triangle 257 is advantageous because it allows for measurements of different portions of the hand including the thickness of the thumb, any of the fingers, the hand, and the thenar of the thumb (the rounded fleshy part of the hand at the base of the thumb). The schematic 200 in the measurement field may require the thickness of the thumb at a predetermined location, a thickness of the hand such as at the inter-phalangeal joint, and a thickness of the thenar of the thumb.

Figure 8F:
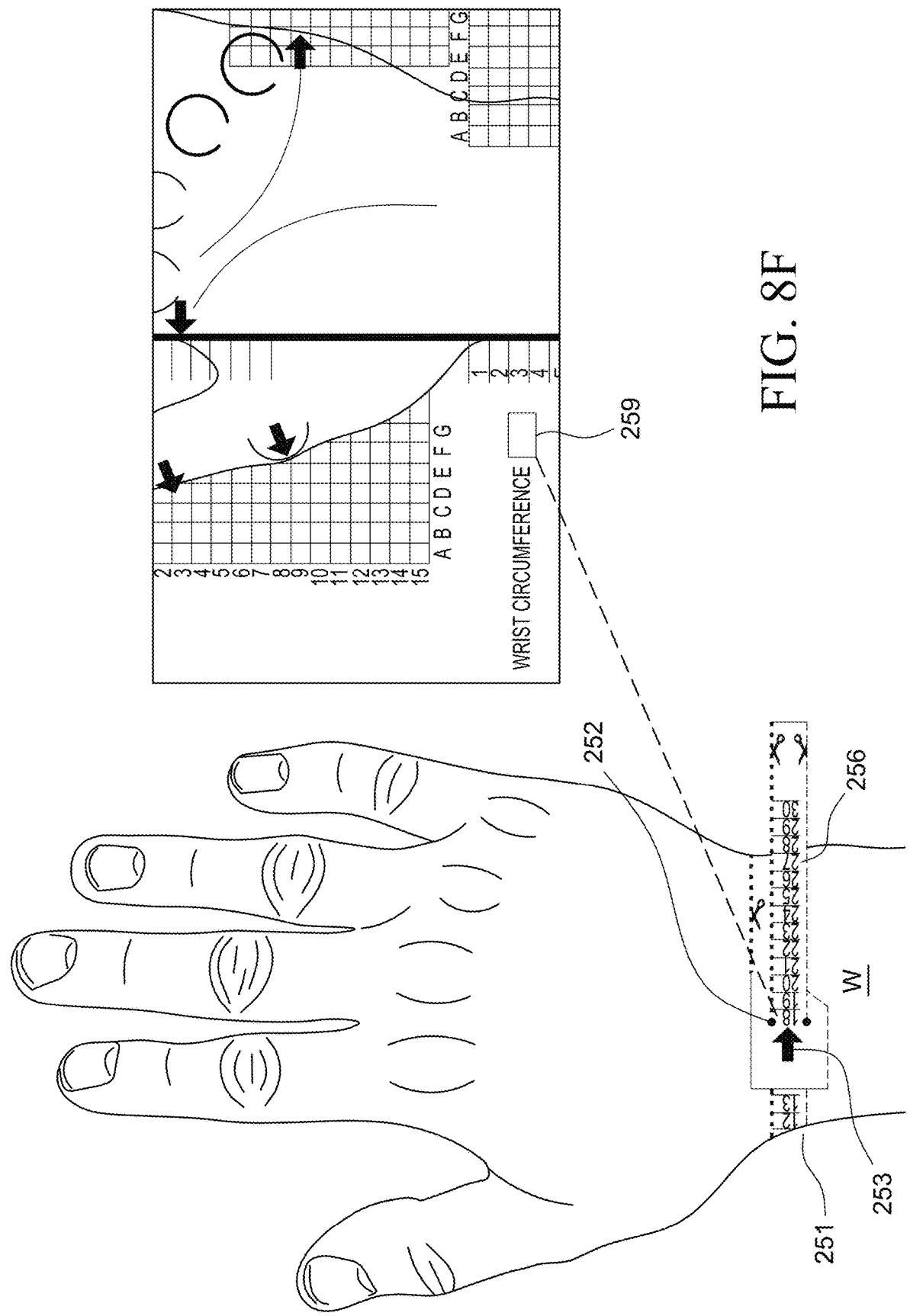
FIG. 8F is an exemplary step of measuring a wrist circumference against a scale from the schematic of FIG. 8A.

FIG. 8F shows how the region 251 is removed from the schematic 200 and used to measure the circumferences of the wrist W. The region 251 is slipped through a slit 252 about the wrist W, so the relative dimension or circumference of the wrist W can be determined by aligning the circumference on the elongate scale 256 to the target 253. The relative dimension according to the elongate scale 256 is entered in a field 259 on the schematic 200.

In an alternative, the schematic 200 is provided by a portable digital device or computer. The portable digital device, such as a tablet, can sense the dimensions of the body part as it is placed on the screen. In yet another alternative, a computer may have a camera that measures the predefined locations on a comparable schematic for entering the measurements.

Figure 9:
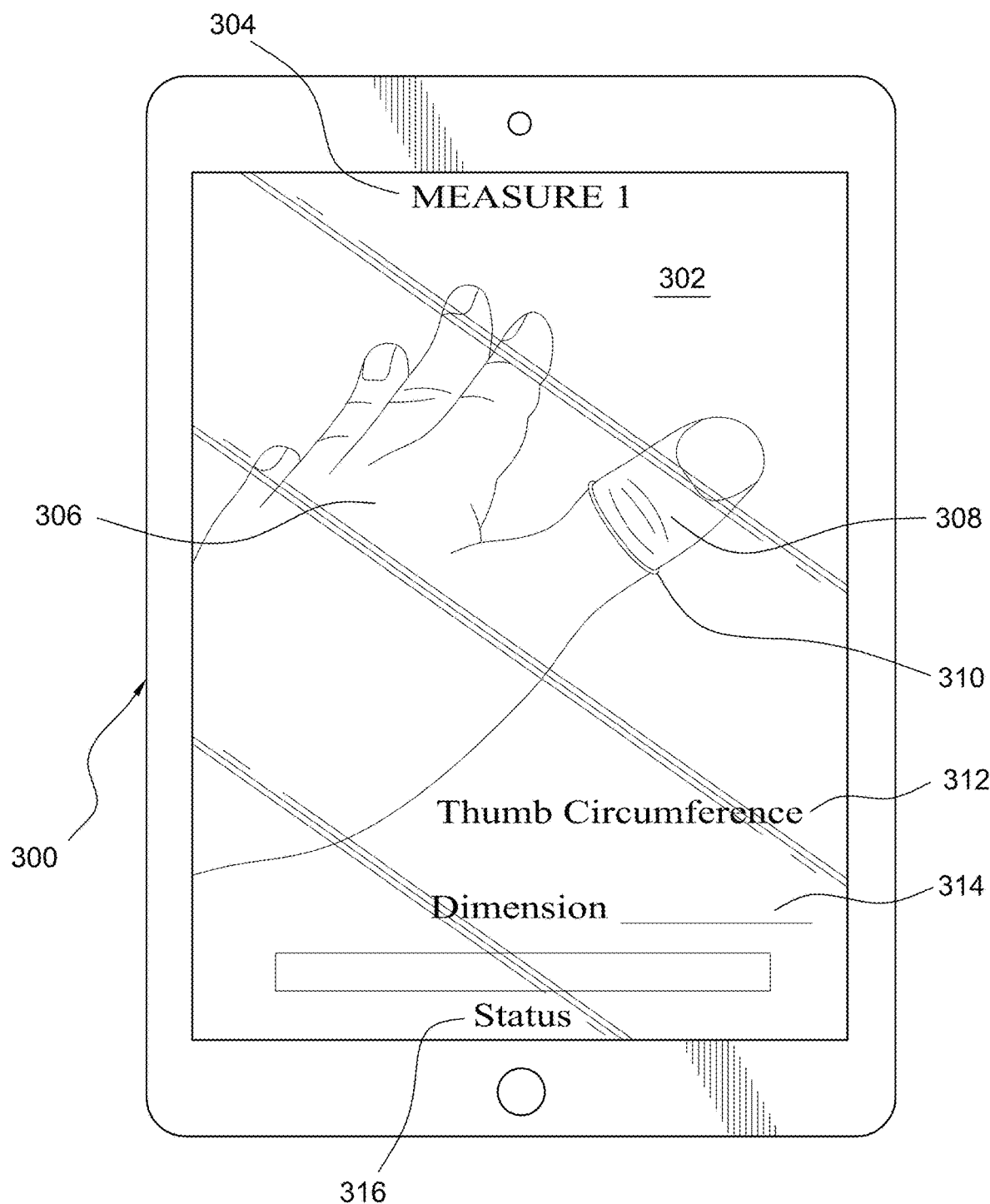
FIG. 9 is an exemplary representation on a device of a data entry system for entering dimensions obtained from the schematic of FIG. 8A.

FIG. 9 exemplifies how the measurements may be entered in an ordering system. In the example of FIG. 9, the measurements are entered by software on a portable digital device 300. The coordinates obtained from the schematic 200 are entered onto a form 302, such as a measurement page by prompting a user to enter a measurement 304 according to one of the at least one array of coordinates in at least one field 312, 314. The body part 306 is depicted to prompt the user where the measurement 304 is found. The form 302 exemplifies a guidance 310 at a location 308 of the measurement on the depicted body part 306. The form 302 specifies the status 316 of the entry of measurements obtained from the schematic 200.

Figures 10A, 10B:
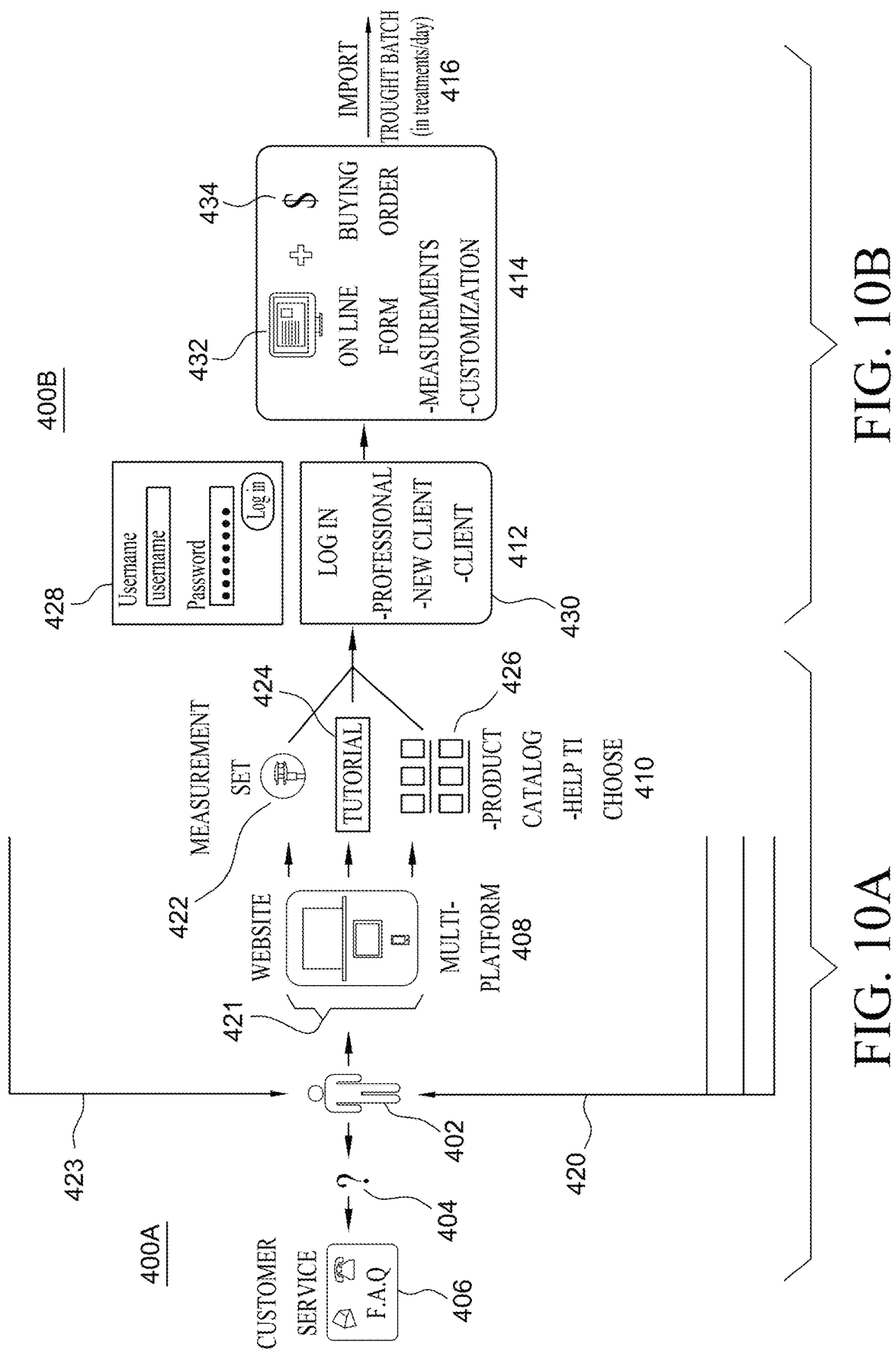
FIG. 10A is an exemplary flow chart depicting a first stage of a system for making the hand brace of FIG. 1.
FIG. 10B is an exemplary flow chart depicting a second stage of a system for making the hand brace of FIG. 1 for use in conjunction with the first stage of FIG. 10A.
Figure 10C:
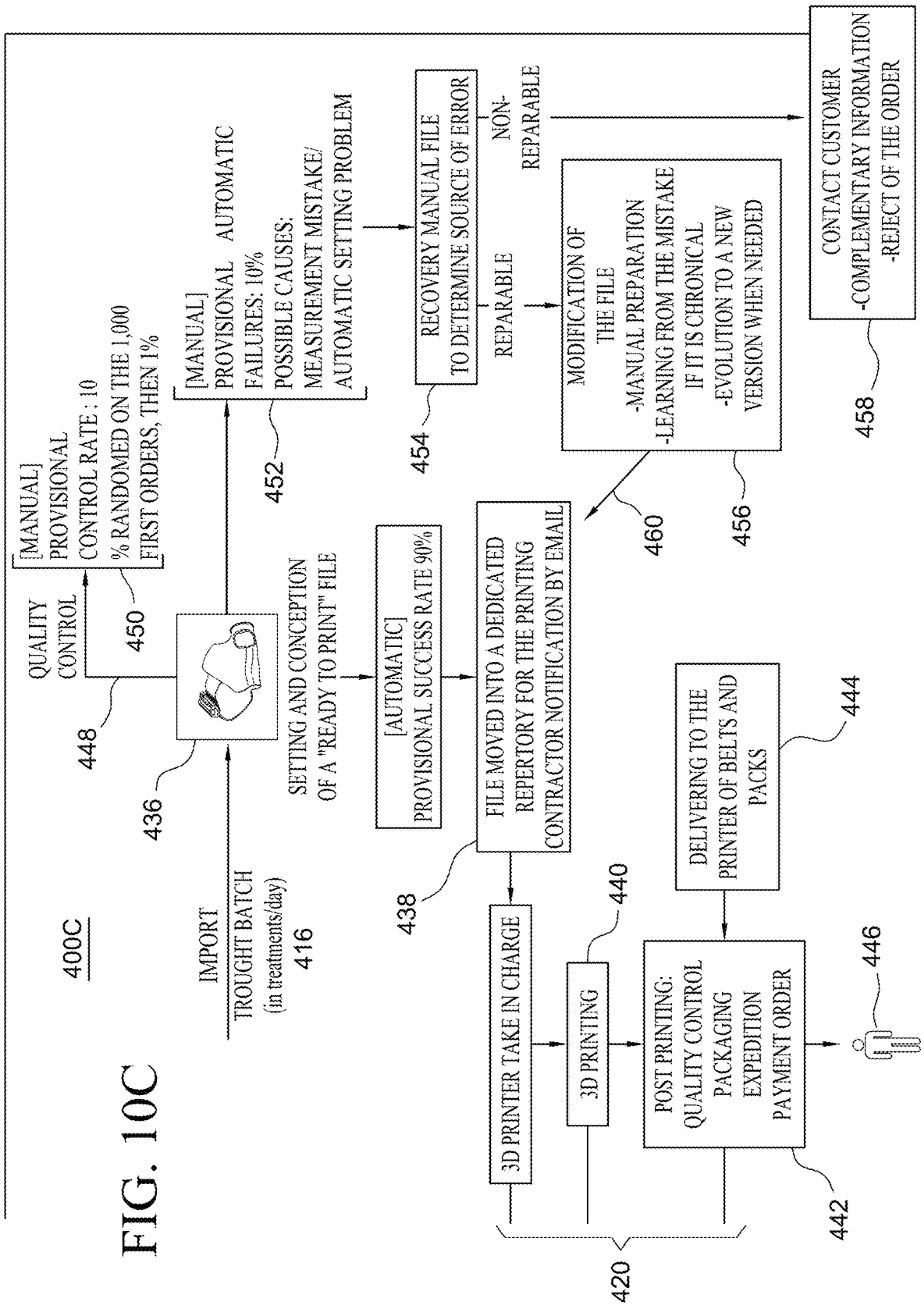
FIG. 10C is an exemplary flow chart depicting a third stage of a system for making the hand brace of FIG. 1 for use in conjunction with the first and second stages of FIGS. 10A and 10B.

FIGS. 10A-10C illustrate an exemplary method for fabricating an orthopedic device. The method involves obtaining at least one measurement 422 of a body part from a user in a step 400A, the step entering the at least one measurement 422 of the body part in an order request 400B, and the step of fabricating the orthopedic device based on the at least one measurement 422 entered into the order request step 400C. A virtual model or digital representation of the user's body part is created 436 upon importing 416 the at least one measurement 422.

According to the step 400A in FIG. 10A, the schematic 200 discussed above is used to measure the dimensions of a user 402. A help system 404 is provided if a clinician has questions on how to proceed with measurement and ordering of the orthopedic device, and there may be live support 406 enabled through various communication means. The ordering system 408 of the orthopedic device may be conducted through a website or other electronic portal based on many known platforms 421 and with client contact 423. The ordering system 408 may include a tutorial 424 for showing how to obtain the at least one measurement 42 from the user 402, and it will be understood that the step 400A is not limited to measuring according to using the schematic 200 discussed above. The ordering system 408 may require a set up process 410. The ordering system 408 may include a catalog 426 showing different orthopedic devices that may be used according to the method for fabricating the orthopedic device.

Referring to FIG. 10B showing order request step 400B, appropriate login information 428 may be required for making the order. At login, various inquiries 412 may be required for answering to establish the user's information for the orthopedic device. The patient/clinic type 430 may be requested. After login, the measurements are entered 414 for customizing the orthopedic device in measurement form 432, according to the measurements obtained in the step 400A. Once the measurements are entered 414, appropriate purchasing information may be required to complete an order 434. After such information is entered into the ordering system, the information is imported 416 into the manufacturing system according to the step 400C.

FIG. 10C exemplifies step 400C, in that the imported information is used to manufacturing the orthopedic device. The manufacturing process preferably employs additive manufacturing, however the method may be used for other manufacturing processes of an orthopedic device. For sake of this explanation, additive manufacturing will be assumed as the means for manufacturing the orthopedic device.

A virtual model of the orthopedic device is developed from the imported information and prepared for manufacturing an actual orthopedic device 436. The virtual file is sent 438 to a facility or printing mechanism, and the printing mechanism forms the orthopedic device 436 by additive manufacturing 440. Once the orthopedic device 436 is prepared, it is inspected 442. If the orthopedic device 436 passes inspection, there may be post assembly 444 including adding strap, belts, fasteners, and other suitable connectivity features, and therapeutic elements such as heating or cooling patches, padding, packs with analgesics, or other known therapeutic elements. Once completed, the orthopedic device 436 is sent to the clinician or user 446. During the manufacturing process, the clinician or user may check the status of the process to determine when the orthopedic device 436 will be finished 420.

During or when the virtual model of the orthopedic device 436 is created, a quality control feedback 448 is provided for determining whether the measurements are correct according to a virtual model 450 and predetermined criteria 452. The inspection may be done manually by an individual reviewing the virtual model 450 or automatically by software according to the predetermined criteria 452. A decision is made 454 whether any defects in the virtual model 450 are reparable 456 or not 458. If the defects are reparable 456, adjustments are made 460 to the virtual model prior to manufacturing. If the defects are not reparable 458, the clinician and/or user is contacted and new measurements or further consultation is conducted.

The orthopedic device, method and system for making the orthopedic device provide an improvement by more accurately capturing the dimensions and features of a user via a standardized format for measuring a user's affected limb or body part. By obtaining more accurate measurements than existing virtual fittings, the orthopedic device advantageously provides an aesthetically pleasing orthosis with improved pressure distribution, comfort, breathability, and support, enhancing user compliance during treatment and overall treatment outcomes. The system and method further provide an efficient and systematic manufacturing process for fabricating the orthopedic device.

While the foregoing embodiments have been described and shown, alternatives, reversal of parts, and modifications of these embodiments, such as those suggested by others may be made to fall within the scope of the disclosure. Reference characters are provided in the claims for explanatory purposes only and are not intended to limit the scope of the claims or restrict each claim limitation to the element shown in the drawings and identified by the reference character.

The constructions described above and illustrated in the drawings are presented for example only and are not intended to limit the concepts and principles of the present disclosure. As is evident from the foregoing description, certain aspects of the present disclosure are not limited by the details of the examples illustrated, and other modifications and applications, or equivalents thereof, will occur to those skilled in the art. The terms "having" and "including" and similar terms as used in the foregoing specification are used in the sense of "optional" or "may include" and not as "required."

Many changes, modifications, variations and other uses and applications of the present construction will, however, become apparent to those skilled in the art after considering the specification and the accompanying drawings. All such changes, modifications, variations and other uses and applications which do not depart from the spirit and scope of the disclosure are deemed covered by the disclosure limited only by the claims which follow.

The invention claimed is:

1. An orthopedic device, comprising:
a body having a monolithic structure and arranged to form a closed circumference in a secured configuration, the body having a predetermined shape in an unsecured configuration;
wherein the body is formed continuously without interruption from at least one polymeric material;
wherein the body defines a band disposed about a periphery of the body, the band being arranged to enclose at least one fenestration region defining at least first and second fenestrations formed by the body and arranged in a predetermined pattern, the body defining at least one rib extending from the band and being adjacent to the at least one fenestration region, the at least one rib exhibiting greater rigidity than the at least one fenestration region, the body defining a thumb column sized and configured for supporting a thumb;
wherein the band and the at least one rib combine to form a frame that extends around the at least one fenestration region, such that the frame is substantially more rigid than the at least one fenestration region, the frame having a varying width about the periphery of the body;
wherein the body defines an opening bordered by the at least one rib and the band, the opening being greater in size than the at least first and second fenestrations of the at one fenestration regions, the opening being located within a length of the thumb column, the thumb column defining an outlet from which a portion of a distal phalange of the thumb extends, the thumb column defining a lip extending about the opening and having a greater thickness than the at least one rib.

2. The orthopedic device of claim 1, wherein the body defines a strap assembly adapted to place the body in the secured configuration and flexibly tension the body, such that upon release of tension in the strap assembly, the body returns to the predetermined shape;
wherein the body defines a strap assembly adapted to place the body in the secured configuration and flexibly tension the body, such that upon release of tension in the strap assembly, the body returns to the predetermined shape, the strap assembly including a strap extending from a first peripheral side of the body and a bracket defined by the body and located on a second peripheral side of the body opposite the first peripheral side and separated by a clearance, the strap being engageable with the bracket to place the body in the secured configuration.

3. The orthopedic device of claim 1, wherein the band extends about an entirety of the body, including peripheral sides enclosing the at least one fenestration region.

4. The orthopedic device of claim 1, wherein the at least one rib is devoid of fenestrations and defines a solid portion of the at least one polymeric material forming the body.

5. The orthopedic device of claim 1, wherein the at least one rib extends adjacently from and between first and second peripheral edges of the body.

6. The orthopedic device of claim 5, wherein the at least one rib merges into the band located along the first and second peripheral edges, and is adjacent to the at least one fenestration region.

7. The orthopedic device of claim 1, wherein the frame forms at least one strength line for the body to maintain its shape and to border the at least one fenestration region.

8. The orthopedic device of claim 1, wherein the body defines first and second regions, the first region is fixedly arranged at a first angle different from a second angle by which the second region is fixedly arranged and different from the first region.

9. The orthopedic device of claim 1, wherein the body is arranged to flexibly conform and tension about a user because of tensioning of a strap assembly to place the orthopedic device in the secured configuration, wherein in the secured configuration, both the monolithic structure and the at least one polymeric material of the body do not yield to movement of a user over which the body extends.

10. The orthopedic device of claim 1, consisting of the body, the body forming a strap assembly integrally formed from and as part of the body in that the body and the strap assembly are one and the same with one another.

11. The orthopedic device of claim 1, wherein the at least first and second fenestrations have different shapes relative to one another.

12. An orthopedic device, comprising:
a body having a monolithic structure and arranged to form a closed circumference in a secured configuration, the body having a predetermined shape in an unsecured configuration, the body being formed continuously without interruption from at least one polymeric material;
the body forming an opening bordered by first and second sides of the body;
a strap assembly including a strap depending from the first side of the body and arranged to extend across to the second side of the body and connect thereto to form the closed circumference;
wherein the body and strap assembly are formed continuously without interruption from a single piece of at least one polymeric material forming a homogenous structure;
wherein the body defines a thumb column sized and configured for supporting a thumb, the thumb column defining a first region arranged for supporting a thumb metacarpal, and a second region arranged for supporting a thumb proximal phalange including a metacarpal phalangeal joint, an opening being formed along the thumb column within the second region, or between the first and second regions, the first region fixedly arranged at an angle different from an angle by which the second region is fixedly arranged and different from the first region, the angle of the first region being arranged to maintain the thumb metacarpal in a fixed position for abduction and flexion, the thumb column fixedly arranged at an angle relative to a remainder of the body outside the thumb column.

13. The orthopedic device of claim 12, wherein the strap is engageable with a bracket carried by the second side of the body laterally opposed to the first side;

wherein the bracket is integrally and continuously formed from the at least one polymeric material and the monolithic structure forming the body;

wherein engagement of the strap to the bracket places the body in the secured configuration in that an exterior of the body forms a continuous circumference, loop, or closed shape without interruption.

14. The orthopedic device of claim 12, wherein the body is semi-rigid in that the body is arranged to flexibly conform and tension about a user because of tensioning of the strap assembly to place the orthopedic device in the secured configuration, wherein in the secured configuration, both the monolithic structure and the at least one polymeric material the body do not yield to movement of a user over which the body extends.

15. The orthopedic device of claim 12, wherein the body defines a strap assembly adapted to place the body in the secured configuration and flexibly tension the body, such that upon release of tension in the strap assembly, the body returns to the predetermined shape, the strap assembly including a strap extending from a first peripheral side of the body and a bracket defined by the body and located on a second peripheral side of the body opposite the first peripheral side and separated by a clearance, the strap being engageable with the bracket to place the body in a secured configuration.

* * * * *